(12) United States Patent
Ezaki et al.

(10) Patent No.: US 9,666,402 B2
(45) Date of Patent: May 30, 2017

(54) ION GENERATION APPARATUS AND ELECTRIC EQUIPMENT

(71) Applicant: Sharp Kabushiki Kaisha, Osaka-shi, Osaka (JP)

(72) Inventors: Tetsuya Ezaki, Osaka (JP); Yoshinori Sekoguchi, Osaka (JP); Satohiko Yamamoto, Osaka (JP); Tomoaki Takado, Osaka (JP); Keitaro Yamada, Osaka (JP); Satoshi Okano, Osaka (JP)

(73) Assignee: Sharp Kabushiki Kaisha, Sakai (JP)

( * ) Notice: Subject to any disclaimer, the term of this patent is extended or adjusted under 35 U.S.C. 154(b) by 65 days.

(21) Appl. No.: 14/428,460

(22) PCT Filed: Feb. 27, 2014

(86) PCT No.: PCT/JP2014/054940
§ 371 (c)(1),
(2) Date: Mar. 16, 2015

(87) PCT Pub. No.: WO2015/019640
PCT Pub. Date: Feb. 12, 2015

(65) Prior Publication Data
US 2015/0248989 A1    Sep. 3, 2015

(30) Foreign Application Priority Data

Aug. 5, 2013   (JP) ................................ 2013-162634
Feb. 26, 2014  (JP) ................................ 2014-035590

(51) Int. Cl.
*H01J 27/02* (2006.01)
*A61L 9/22* (2006.01)
(Continued)

(52) U.S. Cl.
CPC .............. *H01J 27/022* (2013.01); *A61L 9/22* (2013.01); *H01J 27/26* (2013.01); *H01T 23/00* (2013.01); *H01T 19/04* (2013.01)

(58) Field of Classification Search
CPC ................................ H01T 19/04; H01T 23/00
See application file for complete search history.

(56) References Cited

U.S. PATENT DOCUMENTS

2012/0006996 A1* 1/2012 Nishino .................. H01T 23/00
                                                                 250/395
2012/0162851 A1   6/2012 Sato

FOREIGN PATENT DOCUMENTS

CN        202637556 U     1/2013
JP        2011-014319 A   1/2011
(Continued)

OTHER PUBLICATIONS

Official Communication issued in International Patent Application No. PCT/JP2014/054940, mailed on May 27, 2014.

*Primary Examiner* — Nimeshkumar Patel
*Assistant Examiner* — Jacob R Stern
(74) *Attorney, Agent, or Firm* — Keating & Bennett, LLP

(57) ABSTRACT

Each of first to fourth needle-like electrodes is arranged such that a direction of extension thereof is parallel, and generates ions by discharge. Through a space, a gas for conveying the ions generated by the first to fourth needle-like electrodes flows. Needle tips of the first needle-like electrode and the second needle-like electrode protrude from a first wall surface that forms the space, are spaced apart from each other, and are arranged in line in the space. Needle tips of the third needle-like electrode and the fourth needle-like electrode protrude from a second wall surface that forms the space and faces the first wall surface, are spaced apart from each other, and are arranged in line in the space. The first needle-like electrode and the fourth needle-like electrode (Continued)

generate positive ions, and the second needle-like electrode and the third needle-like electrode generate negative ions.

13 Claims, 21 Drawing Sheets

(51) Int. Cl.
*H01J 27/26* (2006.01)
*H01T 23/00* (2006.01)
*H01T 19/04* (2006.01)

(56) References Cited

FOREIGN PATENT DOCUMENTS

| | | | |
|---|---|---|---|
| JP | 2011-060537 A | 3/2011 | |
| JP | 2011-237139 A | 11/2011 | |

\* cited by examiner

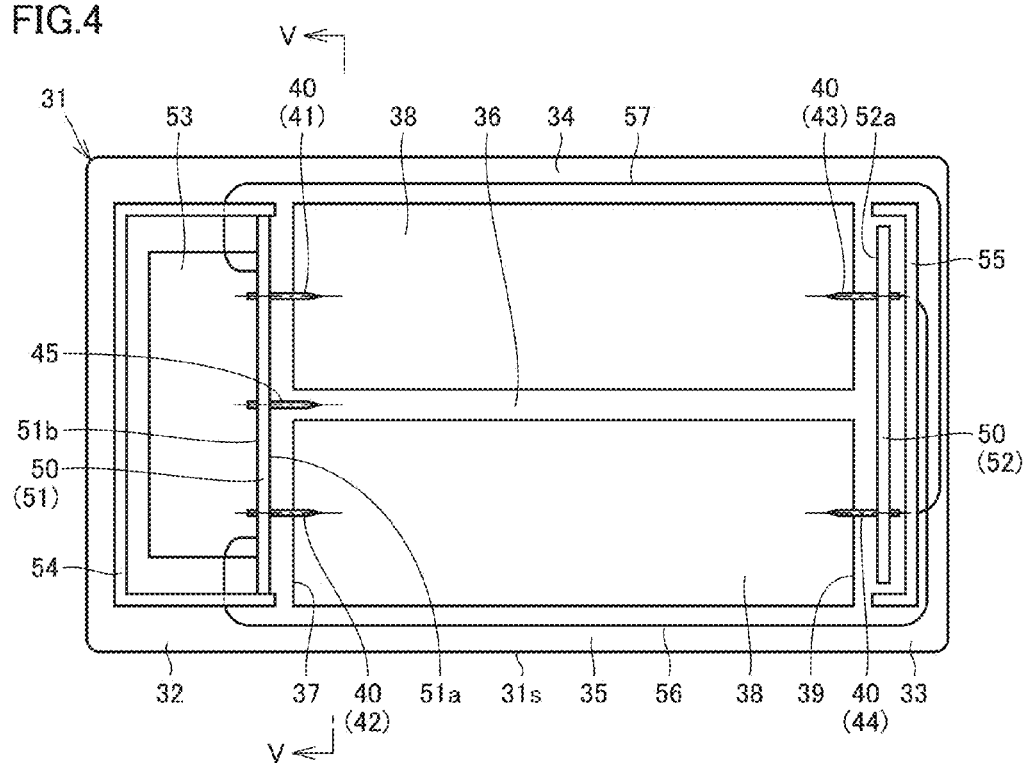
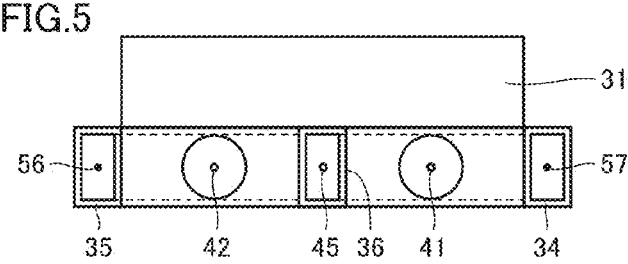

ION GENERATION APPARATUS AND ELECTRIC EQUIPMENT

TECHNICAL FIELD

The present invention relates to an ion generation apparatus and electric equipment, and particularly to an ion generation apparatus including a plurality of needle-like electrodes, and electric equipment using the ion generation apparatus.

BACKGROUND ART

Ion generation apparatuses have conventionally been used for purification, sterilization, deodorization, or the like of air in a room. Many of the ion generation apparatuses generate positive ions and negative ions by corona discharge.

According to a static eliminator described in Japanese Patent Laying-Open No. 2011-14319 (PTD 1), discharge needles are provided such that a longitudinal direction thereof corresponds to a direction orthogonal to an air blowout direction. When a high voltage is applied to these discharge needles and corona discharge occurs, the air around tips of the discharge needles are ionized and the ionized air is blown out by the air blowing operation of a sirocco fan, thereby removing static electricity of an electronic component.

CITATION LIST

Patent Document

PTD 1: Japanese Patent Laying-Open No. 2011-14319

SUMMARY OF INVENTION

Technical Problem

According to the apparatus described in Japanese Patent Laying-Open No. 2011-14319 (PTD 1), a pair of discharge needles for generating ions are arranged on the same wall surface, and a plate-like induction electrode is arranged to face needle tips of the discharge needles. In this case, ions are not generated from the plate-like induction electrode side, and thus, the ions in an air flow path are considered to be unevenly distributed to the discharge needle side. When the sirocco fan or the like is used to blow the air into a room with such uneven ion concentration, it is difficult to obtain a highly-concentrated ion region over a wide range in the room space, even if a high ion concentration is obtained on the side close to the discharge needles.

The present invention has been made in view of the aforementioned problem and a main object of the present invention is to provide an ion generation apparatus that allows a high concentration of positive and negative ions to be present over a wide range.

Solution to Problem

An ion generation apparatus according to one aspect of the present invention includes: discharge electrodes; and an air flow path. The discharge electrodes include first to fourth needle-like electrodes. Each of the first to fourth needle-like electrodes is arranged such that a direction of extension thereof is parallel. Each of the first to fourth needle-like electrodes generates ions by discharge. Through the air flow path, a gas for conveying the ions generated by the discharge electrodes flows. Needle tips of the first needle-like electrode and the second needle-like electrode protrude from a first wall surface that forms the air flow path, are spaced apart from each other by a first interval, and are arranged in line in the air flow path. Needle tips of the third needle-like electrode and the fourth needle-like electrode protrude from a second wall surface that forms the air flow path and faces the first wall surface, are spaced apart from each other by a second interval, and are arranged in line in the air flow path. The first needle-like electrode and the fourth needle-like electrode generate positive ions, and the second needle-like electrode and the third needle-like electrode generate negative ions.

Preferably, in the aforementioned ion generation apparatus, the needle tip of the first needle-like electrode and the needle tip of the third needle-like electrode face each other. Preferably, a distance between the needle tip of the first needle-like electrode and the needle tip of the third needle-like electrode is larger than the first interval and larger than the second interval.

Preferably, in the aforementioned ion generation apparatus, the needle tip of the second needle-like electrode and the needle tip of the fourth needle-like electrode face each other. Preferably, a distance between the needle tip of the second needle-like electrode and the needle tip of the fourth needle-like electrode is larger than the first interval and larger than the second interval.

Preferably, the ion generation apparatus further includes: a base member having the discharge electrodes mounted thereon; and a casing that houses the base member. A part of an outer surface of the casing forms the first wall surface and the second wall surface. The casing is provided such that the air flow path is formed between the first wall surface and the second wall surface. Preferably, the air flow path is formed to pass through the casing. Preferably, the base member includes a first base member and a second base member provided separately. The first needle-like electrode and the second needle-like electrode are mounted on the first base member, and the third needle-like electrode and the fourth needle-like electrode are mounted on the second base member.

Preferably, the ion generation apparatus further includes: a boosting transformer; and an induction electrode. One end on the secondary winding side of the boosting transformer is electrically connected to the first to fourth needle-like electrodes, and the boosting transformer generates a positive or negative high voltage applied to each of the first to fourth needle-like electrodes. The induction electrode is electrically connected to the other end on the secondary winding side of the boosting transformer. Preferably, the induction electrode is arranged between the first needle-like electrode and the second needle-like electrode and at a distance from both the first needle-like electrode and the second needle-like electrode.

Electric equipment according to one aspect of the present invention includes: the ion generation apparatus according to any one of the aforementioned aspects; and an air blower for blowing a gas into an air flow path of the ion generation apparatus.

Electric equipment according to another aspect of the present invention includes: discharge electrodes; and an air flow path. The discharge electrodes include first to fourth needle-like electrodes. Each of the first to fourth needle-like electrodes is arranged such that a direction of extension thereof is parallel. Each of the first to fourth needle-like electrodes generates ions by discharge. Through the air flow path, a gas for conveying the ions generated by the discharge electrodes flows. Needle tips of the first needle-like electrode and the second needle-like electrode protrude from a first wall surface that forms the air flow path, are spaced apart from each other by a first interval, and are arranged in line in the air flow path. Needle tips of the third needle-like electrode and the fourth needle-like electrode protrude from a second wall surface that forms the air flow path and faces the first wall surface, are spaced apart from each other by a second interval, and are arranged in line in the air flow path. The first needle-like electrode and the fourth needle-like electrode generate positive ions, and the second needle-like electrode and the third needle-like electrode generate negative ions.

An ion generation apparatus according to another aspect of the present invention includes: an air flow path through which a gas flows; and first to fourth needle-like electrodes. Each of the first to fourth needle-like electrodes is arranged to extend in a direction orthogonal to a gas flowing direction in the air flow path, and generates ions by discharge. The first needle-like electrode and the second needle-like electrode protrude into the air flow path from a first wall surface that forms the air flow path. The third needle-like electrode and the fourth needle-like electrode protrude into the air flow path from a second wall surface that forms the air flow path and faces the first wall surface. The first needle-like electrode and the second needle-like electrode are arranged such that needle tips thereof are spaced apart from each other by a first distance in the direction orthogonal to the gas flowing direction in the air flow path. The first needle-like electrode and the third needle-like electrode are arranged such that needle tips thereof face each other and are spaced apart from each other by a second distance in the direction orthogonal to the gas flowing direction in the air flow path. On the downstream side of the gas flow with respect to the first to fourth needle-like electrodes, the air flow path has a bifurcated duct bifurcated in the direction of the longer one of the first distance and the second distance.

Preferably, in the aforementioned ion generation apparatus, one of the two needle-like electrodes that form the shorter one of the first distance and the second distance generates positive ions, and the other generates negative ions.

Preferably, in the aforementioned ion generation apparatus, the first to fourth needle-like electrodes are integrated into one unit. Preferably, the ion generation apparatus includes a plurality of sets of the first to fourth needle-like electrodes integrated into one unit.

Preferably, the aforementioned ion generation apparatus further includes a partition plate for partitioning the two needle-like electrodes that form the shorter one of the first distance and the second distance.

ADVANTAGEOUS EFFECTS OF INVENTION

According to the ion generation apparatus of the present invention, it is possible to cause a high concentration of positive and negative ions to be present over a wide range.

BRIEF DESCRIPTION OF DRAWINGS

FIG. 4 is a plan view showing an internal structure of the ion generation apparatus according to the first embodiment.

FIG. 5 is a cross-sectional view of the ion generation apparatus taken along line V-V shown in FIG. 4.

DESCRIPTION OF EMBODIMENTS

Figure 1:
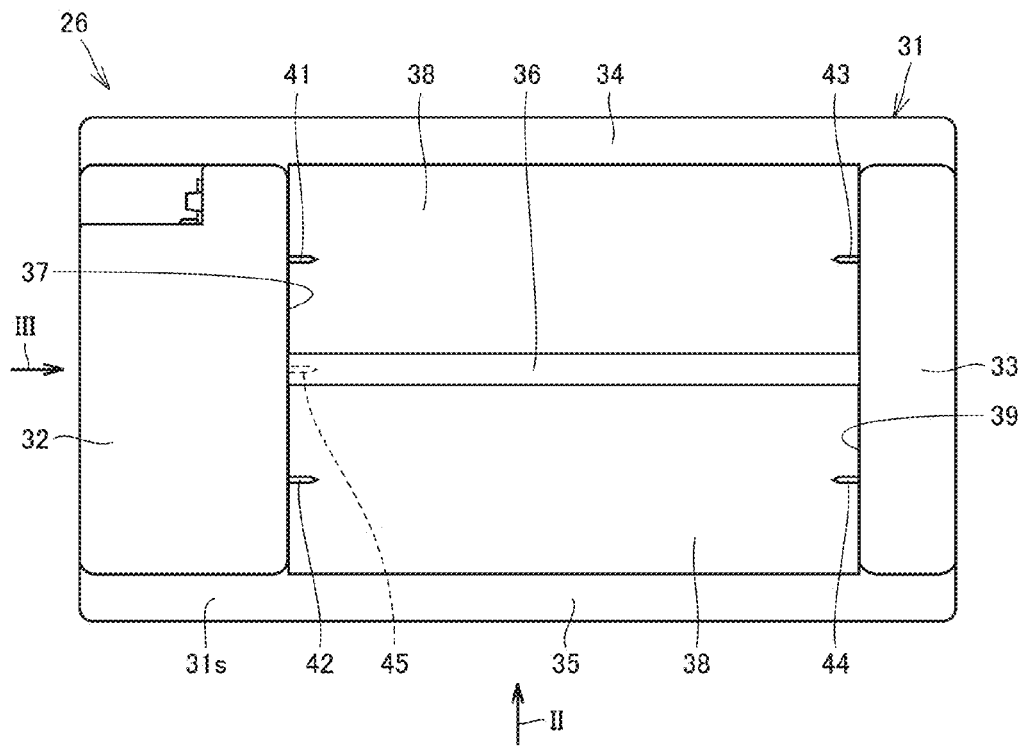
FIG. 1 is a plan view showing a configuration of an ion generation apparatus according to a first embodiment of the present invention.

Embodiments of the present invention will be described hereinafter with reference to the drawings. In the following drawings, the same or corresponding portions are indicated by the same reference numerals, and description thereof will not be repeated.

(First Embodiment)

Figure 2:
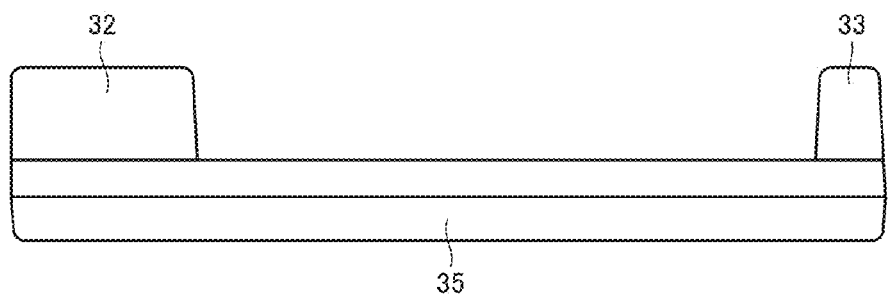
FIG. 2 is a side view showing the ion generation apparatus viewed from a direction shown by an arrow II in FIG. 1.
Figure 3:
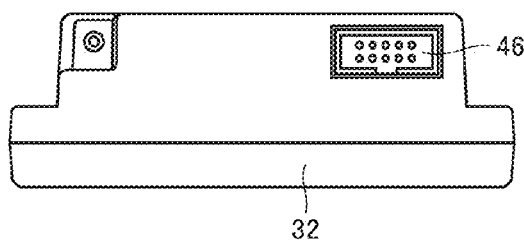
FIG. 3 is a side view showing the ion generation apparatus viewed from a direction shown by an arrow III in FIG. 1.

FIG. 1 is a plan view showing a configuration of an ion generation apparatus 26 according to a first embodiment of the present invention. FIG. 2 is a side view showing ion generation apparatus 26 viewed from a direction shown by an arrow II in FIG. 1. FIG. 3 is a side view showing ion generation apparatus 26 viewed from a direction shown by an arrow III in FIG. 1. FIG. 4 is a plan view showing an internal structure of ion generation apparatus 26 according to the first embodiment. FIG. 5 is a cross-sectional view of ion generation apparatus 26 taken along line V-V shown in FIG. 4. A structure of ion generation apparatus 26 according to the first embodiment will be first described in detail with reference to FIGS. 1 to 5.

Ion generation apparatus 26 according to the first embodiment mainly includes an outer case 31, a discharge electrode 40, an induction electrode (counter electrode) 45, a base member 50, a high voltage generation circuit portion 53, a substrate supporting case 54 and a substrate supporting case 55, and a wiring 56 and a wiring 57.

Discharge electrode 40 includes a first needle-like electrode 41, a second needle-like electrode 42, a third needle-like electrode 43, and a fourth needle-like electrode 44. Each of first to fourth needle-like electrodes 41 to 44 is formed to have a needle shape, extends linearly and has a sharp-pointed needle tip. First to fourth needle-like electrodes 41 to 44 are arranged in the same plane such that the directions of extension of the respective electrodes are parallel to one another.

First needle-like electrode 41 and second needle-like electrode 42 are arranged in line in a direction orthogonal to the directions of extension of the respective electrodes, and are spaced apart from each other. Third needle-like electrode 43 and fourth needle-like electrode 44 are arranged in line in a direction orthogonal to the directions of extension of the respective electrodes, and are spaced apart from each other.

First needle-like electrode 41 and third needle-like electrode 43 are arranged in the directions of extension of the respective electrodes to face each other, and are spaced apart from each other. The needle tip of first needle-like electrode 41 and the needle tip of third needle-like electrode 43 face each other. A central axis of first needle-like electrode 41 and a central axis of third needle-like electrode 43 are located on the same straight line. Second needle-like electrode 42 and fourth needle-like electrode 44 are arranged in the directions of extension of the respective electrodes to face each other, and are spaced apart from each other. The needle tip of second needle-like electrode 42 and the needle tip of fourth needle-like electrode 44 face each other. A central axis of second needle-like electrode 42 and a central axis of fourth needle-like electrode 44 are located on the same straight line.

Induction electrode 45 is arranged between first needle-like electrode 41 and second needle-like electrode 42. Induction electrode 45 is spaced apart from both first needle-like electrode 41 and second needle-like electrode 42. Induction electrode 45 is provided at a position where a distance between first needle-like electrode 41 and induction electrode 45 is equal to a distance between second needle-like electrode 42 and induction electrode 45. Induction electrode 45 is also provided at a position where a distance between third needle-like electrode 43 and induction electrode 45 is equal to a distance between fourth needle-like electrode 44 and induction electrode 45.

Each of first to fourth needle-like electrodes 41 to 44 generates ions by discharge. First needle-like electrode 41 and fourth needle-like electrode 44 generate positive ions. Second needle-like electrode 42 and third needle-like electrode 43 generate negative ions. First needle-like electrode 41 and third needle-like electrode 43 generate the ions of opposite polarities, and second needle-like electrode 42 and fourth needle-like electrode 44 generate the ions of opposite polarities. First needle-like electrode 41 and second needle-like electrode 42 generate the ions of opposite polarities, and third needle-like electrode 43 and fourth needle-like electrode 44 generate the ions of opposite polarities.

High voltage generation circuit portion 53 generates a high voltage applied to first to fourth needle-like electrodes 41 to 44. When the positive high voltage is applied to first needle-like electrode 41 and the negative high voltage is applied to second needle-like electrode 42, corona discharge occurs between these discharge electrodes and induction electrode 45, and thus, the positive ions and the negative ions are generated. Similarly, when the negative high voltage is applied to third needle-like electrode 43 and the positive high voltage is applied to fourth needle-like electrode 44, corona discharge occurs between these discharge electrodes and induction electrode 45, and thus, the negative ions and the positive ions are generated.

Base member 50 has discharge electrodes 40 mounted thereon. Base member 50 includes, as separate base members, a substrate 51 which is a first base member, and a substrate 52 which is a second base member. Substrate 51 and substrate 52 are provided to face each other. Substrate 51 has one surface 51a and the other surface 51b, and substrate 52 has one surface 52a. Substrates 51 and 52 are arranged such that surface 51a and surface 52a face each other.

First needle-like electrode 41 and second needle-like electrode 42 are mounted on substrate 51. First needle-like electrode 41 and second needle-like electrode 42 are fixed to substrate 51 such that the needle tips thereof protrude from surface 51a. Third needle-like electrode 43 and fourth needle-like electrode 44 are mounted on substrate 52. Third needle-like electrode 43 and fourth needle-like electrode 44 are fixed to substrate 52 such that the needle tips thereof protrude from surface 52a.

High voltage generation circuit portion 53 is provided on the other surface 51b of substrate 51. Substrate supporting case 54 is provided to support substrate 51 and cover high voltage generation circuit portion 53. Substrate supporting case 55 is provided to support substrate 52.

Wiring 56 is provided as a connection member for electrically connecting high voltage generation circuit portion 53 and third needle-like electrode 43. Wiring 57 is provided as a connection member for electrically connecting high voltage generation circuit portion 53 and fourth needle-like electrode 44. Substrate supporting case 55 is provided to cover contact points between third and fourth needle-like electrodes 43 and 44 and wirings 56 and 57 on substrate 52. Instead of such a configuration that single substrate supporting case 55 shown in FIG. 4 covers both of the two contact points between third and fourth needle-like electrodes 43 and 44 and wirings 56 and 57, a case that covers the contact point between third needle-like electrode 43 and wiring 56 and a case that covers the contact point between fourth needle-like electrode 44 and wiring 57 may be provided separately.

Outer case 31 is provided as a casing that forms an appearance of ion generation apparatus 26. Outer case 31 is integrally molded from a resin material. Outer case 31 has, as components thereof, substrate housing portions 32 and 33, and rib-like portions 34 to 36. Outer case 31 has a rectangular frame shape whose four sides is formed by substrate housing portion 32, rib-like portion 35, substrate housing portion 33, and rib-like portion 34. Outer case 31 has a rectangular two-dimensional view having a long side extending along the direction of extension of discharge electrode 40 and a short side extending along the direction orthogonal to the direction of extension of discharge electrode 40.

Substrate housing portion 32 and substrate housing portion 33 are spaced apart from each other and are arranged in parallel. Substrate housing portion 32 has a capacity larger than that of substrate housing portion 33. Substrate 51, high voltage generation circuit portion 53 and substrate supporting case 54 are housed in substrate housing portion 32. Substrate 52 and substrate supporting case 55 are housed in substrate housing portion 33. First needle-like electrode 41 and second needle-like electrode 42 extend from surface 51a of substrate 51 to outside outer case 31. Third needle-like electrode 43 and fourth needle-like electrode 44 extend from surface 52a of substrate 52 to outside outer case 31. In addition to the configuration shown in FIG. 4, protective covers for preventing direct touch on the needle tips of first to fourth needle-like electrodes 41 to 44 may be provided to improve the safety.

First and second needle-like electrodes 41 and 42, induction electrode 45, substrate 51, high voltage generation circuit portion 53, and substrate supporting case 54 form a power supply unit. Third and fourth needle-like electrodes 43 and 44, substrate 52 and substrate supporting case 55 form an electrode unit.

Substrate 51 having first and second needle-like electrodes 41 and 42 mounted thereon and substrate 52 having third and fourth needle-like electrodes 43 and 44 mounted thereon are both housed in outer case 31. As a result, first to fourth needle-like electrodes 41 to 44 are integrated into one unit. Furthermore, high voltage generation circuit portion 53, induction electrode 45 and wirings 56 and 57 are also housed in outer case 31. The elements that form ion generation apparatus 26 are housed in outer case 31 and are integrated.

Rib-like portion 34 and rib-like portion 35 are spaced apart from each other and are arranged in parallel to be orthogonal to substrate housing portion 32 and substrate housing portion 33. One ends of substrate housing portion 32 and substrate housing portion 33 that face each other are coupled by rib-like portion 34. The other ends of substrate housing portion 32 and substrate housing portion 33 that face each other are coupled by rib-like portion 35.

Rib-like portion 36 is arranged in parallel with rib-like portion 34 and rib-like portion 35. Between rib-like portion 34 and rib-like portion 35, rib-like portion 36 couples substrate housing portion 32 and substrate housing portion 33.

Rib-like portions 34 to 36 extend linearly from substrate housing portion 32 along the directions of extension of first needle-like electrode 41 and second needle-like electrode 42. Rib-like portions 34 to 36 extend linearly from substrate housing portion 33 along the directions of extension of third needle-like electrode 43 and fourth needle-like electrode 44.

Induction electrode 45 protrudes from surface 51a of substrate 51 into rib-like portion 36. A tip portion of induction electrode 45 is housed in outer case 31 (rib-like portion 36). Induction electrode 45 may have a plate-like or bar-like shape, instead of the needle-like shape shown in the figures.

Wiring 56 is routed to extend from substrate housing portion 32 through rib-like portion 35 to substrate housing portion 33. Wiring 57 is routed to extend from substrate housing portion 32 through rib-like portion 34 to substrate housing portion 33. Wiring 56 is routed to run through one of rib-like portion 34 and rib-like portion 35, and wiring 57 is routed to run through the other of rib-like portion 34 and rib-like portion 35.

A hollow space 38 is formed inside outer case 31 surrounded by substrate housing portion 32, rib-like portion 35, substrate housing portion 33, and rib-like portion 34. Space 38 is formed to have a shape passing through outer case 31 in a direction perpendicular to the drawing sheets of FIGS. 1 and 4, i.e., in a vertical direction in FIGS. 2, 3 and 5.

Outer case 31 has an outer surface 31s, and a part of outer surface 31s forms a first wall surface 37 and a second wall surface 39 that faces first wall surface 37. First wall surface 37 is formed on substrate housing portion 32, and second wall surface 39 is formed on substrate housing portion 33. First wall surface 37 and second wall surface 39 form a part of a perimeter of space 38. Space 38 between substrate housing portions 32 and 33 is bounded by first wall surface 37 and second wall surface 39. Space 38 is formed between first wall surface 37 and second wall surface 39.

The tip portions of first to fourth needle-like electrodes 41 to 44 extending from substrates 51 and 52 are arranged in space 38. The needle tips of first needle-like electrode 41 and second needle-like electrode 42 protrude from first wall surface 37 to outside outer case 31, and are arranged in line in space 38. The needle tips of third needle-like electrode 43 and fourth needle-like electrode 44 protrude from second wall surface 39 to outside outer case 31, and are arranged in line in space 38. The needle tips of first needle-like electrode 41 and third needle-like electrode 43 are arranged in space 38 between rib-like portion 34 and rib-like portion 36, and the needle tips of second needle-like electrode 42 and fourth needle-like electrode 44 are arranged in space 38 between rib-like portion 36 and rib-like portion 35.

First wall surface 37 has an opening passing through outer case 31 in a thickness direction, and this opening allows an internal space of substrate housing portion 32 to communicate with space 38. First needle-like electrode 41 and second needle-like electrode 42 pass through the openings formed in first wall surface 37, and are arranged with the needle tips thereof exposed to space 38. Second wall surface 39 has an opening passing through outer case 31 in the thickness direction, and this opening allows an internal space of substrate housing portion 33 to communicate with space 38. Third needle-like electrode 43 and fourth needle-like electrode 44 pass through the openings formed in second wall surface 39, and are arranged with the needle tips thereof exposed to space 38.

The air is flown through space 38. Outer case 31 defines a part of a flow path of the air. The ions generated by discharge electrode 40 are conveyed by the air flowing through space 38. Space 38 forms a part of an air flow path through which a gas for conveying the ions generated by discharge electrode 40 flows. First wall surface 37 and second wall surface 39 that define an outer perimeter of space 38 form a part of the air flow path.

The air flowing through space 38 is flown in the direction perpendicular to the drawing sheets of FIGS. 1 and 4, i.e., in the vertical direction in FIGS. 2, 3 and 5. First to fourth needle-like electrodes 41 to 44 are arranged on the same plane orthogonal to the direction of the air flow in space 38. First to fourth needle-like electrodes 41 to 44 extend in the direction orthogonal to the direction of the air flow in space 38, and are arranged in parallel with one another.

Ion generation apparatus 26 further includes a power feeding connector 46. Power feeding connector 46 is provided in substrate housing portion 32 that houses high voltage generation circuit portion 53. Power feeding connector 46 is provided as a power feeding portion for supplying electric power to high voltage generation circuit portion 53.

Figure 6:
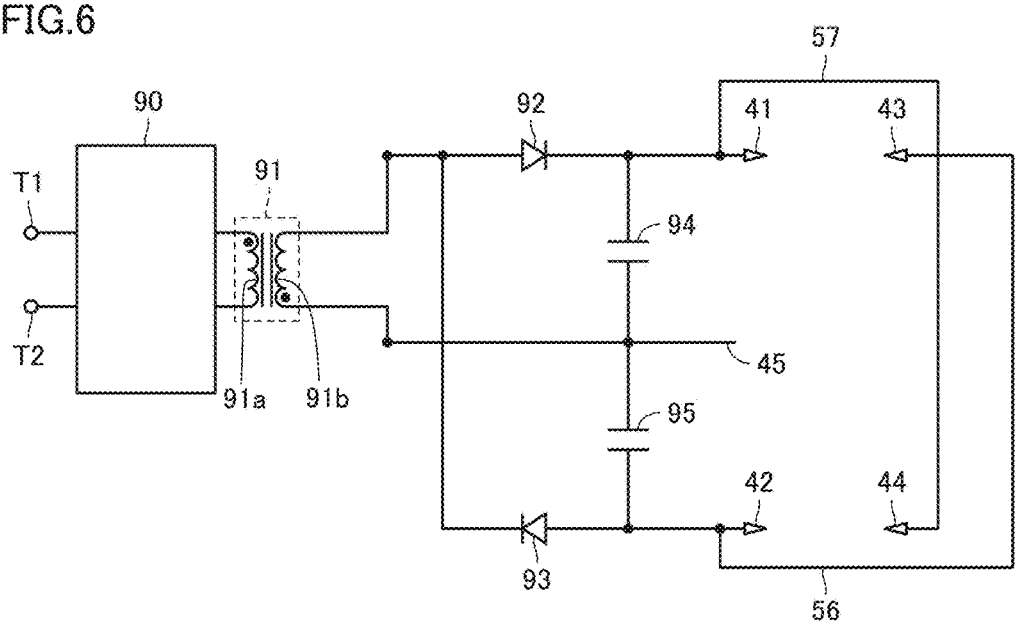
FIG. 6 is a circuit diagram showing the configuration of the ion generation apparatus according to the first embodiment.

FIG. 6 is a circuit diagram showing the configuration of ion generation apparatus 26 according to the first embodiment. As shown in FIG. 6, ion generation apparatus 26 includes terminals T1 and T2, a boosting circuit 90, a boosting transformer 91, diodes 92 and 93, and capacitors 94 and 95, in addition to first to fourth needle-like electrodes 41 to 44 and induction electrode 45. Boosting circuit 90, boosting transformer 91, diodes 92 and 93, and capacitors 94 and 95 are included in the configuration of high voltage generation circuit portion 53 shown in FIG. 4.

Boosting circuit 90 is configured to include a diode, a resistive element, an NPN bipolar transistor and the like as appropriate. Boosting transformer 91 includes a primary winding 91a and a secondary winding 91b. Diodes 92 and 93 and capacitors 94 and 95 are provided for rectification. One end of secondary winding 91b is electrically connected to first to fourth needle-like electrodes 41 to 44, and the other end of secondary winding 91b is electrically connected to induction electrode 45.

Boosting transformer 91 generates the positive or negative high voltage applied to each of first to fourth needle-like electrodes 41 to 44. When the voltage is applied between terminals T1 and T2, a positive high-voltage pulse is applied through diode 92 to first needle-like electrode 41 and fourth needle-like electrode 44, and a negative high-voltage pulse is applied through diode 93 to second needle-like electrode 42 and third needle-like electrode 43. As a result, corona discharge occurs between the needle tips of first to fourth needle-like electrodes 41 to 44 and induction electrode 45. Thus, first needle-like electrode 41 and fourth needle-like electrode 44 generate the positive ions, and second needle-like electrode 42 and third needle-like electrode 43 generate the negative ions.

The positive ions are cluster ions in each of which a plurality of water molecules are attached to a hydrogen ion ($H^+$), and are represented by $H^+(H_2O)m$ (m is an arbitrary integer equal to or larger than 0). The negative ions are cluster ions in each of which a plurality of water molecules are attached to an oxygen ion ($O_2^-$), and are represented by $O_2^-(H_2O)n$ (n is an arbitrary integer equal to or larger than 0).

When the positive ions and the negative ions are emitted, both ions surround fungi and viruses floating in the air, and a chemical reaction occurs on the surfaces thereof. At this time, hydroxyl radicals (.OH), which are active species, are generated and the floating fungi and the like can be eliminated as a result of the reaction of the hydroxyl radicals.

Figure 7:
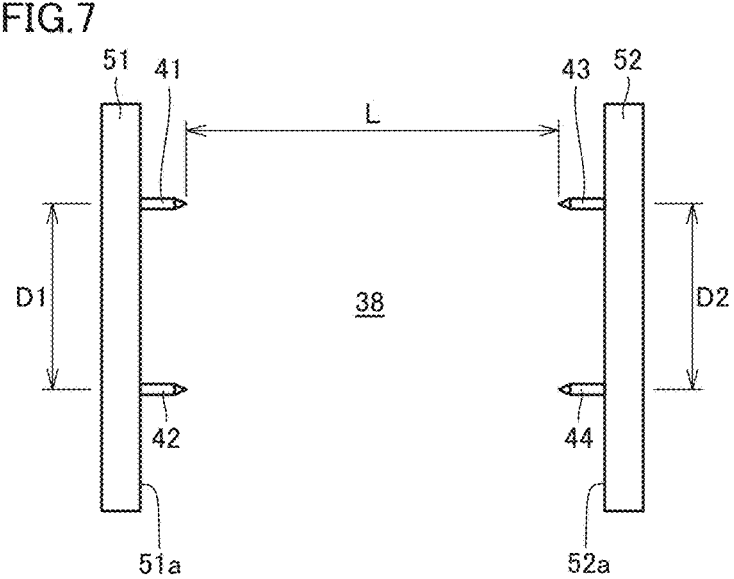
FIG. 7 is a schematic view showing arrangement of discharge electrodes of the ion generation apparatus according to the first embodiment.

FIG. 7 is a schematic view showing arrangement of discharge electrodes 40 of ion generation apparatus 26 according to the first embodiment. The arrangement of discharge electrodes 40 according to the first embodiment, i.e., first to fourth needle-like electrodes 41 to 44 will be described with reference to FIG. 7. For the sake of simplification, FIG. 7 shows only first to fourth needle-like electrodes 41 to 44, substrate 51 having first and second needle-like electrodes 41 and 42 mounted thereon, and substrate 52 having third and fourth needle-like electrodes 43 and 44 mounted thereon.

First and second needle-like electrodes 41 and 42 are arranged on the same plane in the direction orthogonal to the direction of the air flow in space 38 (i.e., the direction perpendicular to the drawing sheet of FIG. 7), such that the directions of extension of the respective electrodes are parallel. The needle tips of first and second needle-like electrodes 41 and 42 are spaced apart from each other by a first interval D1 and are arranged in line in space 38. First and second needle-like electrodes 41 and 42 are arranged such that the needle tips thereof are spaced apart from each other by first interval D1.

Third and fourth needle-like electrodes 43 and 44 are arranged on the same plane in the direction orthogonal to the direction of the air flow in space 38, such that the directions of extension of the respective electrodes are parallel. The needle tips of third and fourth needle-like electrodes 43 and 44 are spaced apart from each other by a second interval D2 and are arranged in line in space 38. Third and fourth needle-like electrodes 43 and 44 are arranged such that the needle tips thereof are spaced apart from each other by second interval D2.

First and third needle-like electrodes 41 and 43 are arranged such that the directions of extension of the respective electrodes are on the same straight line in the direction orthogonal to the direction of the air flow in space 38. The needle tips of first and third needle-like electrodes 41 and 43 are spaced apart from each other by a distance L and are arranged in space 38. First and third needle-like electrodes 41 and 43 are arranged such that the needle tips thereof are spaced apart from each other by distance L.

Second and fourth needle-like electrodes 42 and 44 are arranged such that the directions of extension of the respective electrodes are on the same straight line in the direction orthogonal to the direction of the air flow in space 38. The needle tips of second and fourth needle-like electrodes 42 and 44 are spaced apart from each other by distance L and are arranged in space 38. Second and fourth needle-like electrodes 42 and 44 are arranged such that the needle tips thereof are spaced apart from each other by distance L.

Surface 51a of substrate 51 is parallel to surface 52a of substrate 52, and first and second needle-like electrodes 41 and 42 protrude vertically by the same distance with respect to surface 51a, and third and fourth needle-like electrodes 43 and 44 protrude vertically by the same distance with respect to surface 52a. As a result of this arrangement, the distance between the needle tips of first and third needle-like electrodes 41 and 43 is equal to the distance between the needle tips of second and fourth needle-like electrodes 42 and 44.

Distance L between the needle tip of first needle-like electrode 41 and the needle tip of third needle-like electrode 43 is larger than interval D1 between first needle-like electrode 41 and second needle-like electrode 42, and is larger than interval D2 between third needle-like electrode 43 and fourth needle-like electrode 44. Distance L between the needle tip of second needle-like electrode 42 and the needle tip of fourth needle-like electrode 44 is larger than interval D1 between first needle-like electrode 41 and second needle-like electrode 42, and is larger than interval D2 between third needle-like electrode 43 and fourth needle-like electrode 44.

First needle-like electrode 41 and second needle-like electrode 42 form interval D1 which is the shorter one of interval D1 and distance L. One of the two needle-like electrodes that form interval D1 is first needle-like electrode 41 that generates the positive ions, and the other is second needle-like electrode 42 that generates the negative ions. Rib-like portion 36 of outer case 31 has a function as a partition plate for partitioning the two needle-like electrodes, i.e., first needle-like electrode 41 and second needle-like electrode 42, that form interval D1 which is the shorter one of interval D1 and distance L.

Figure 8:
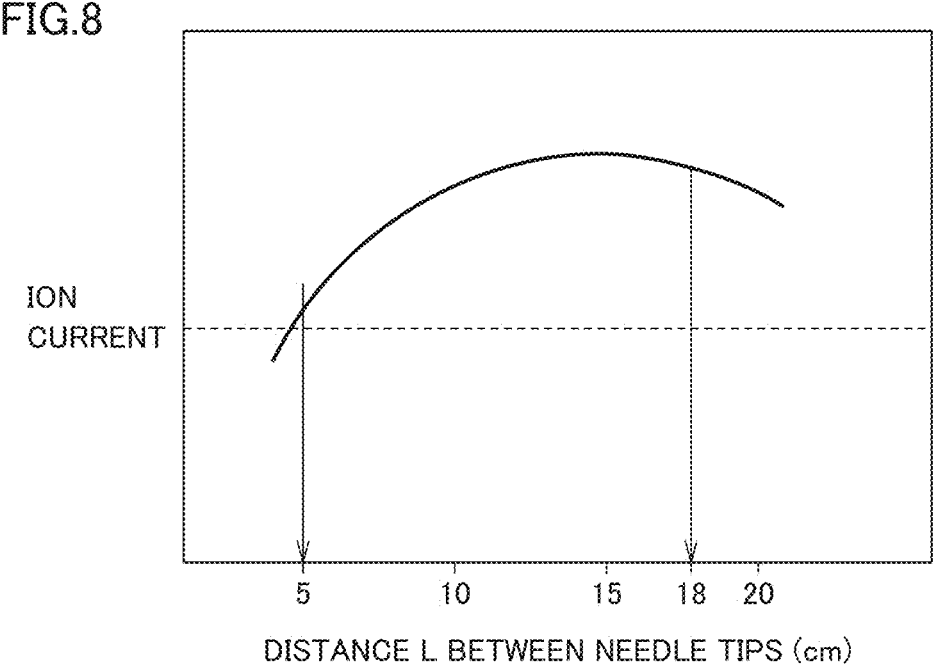
FIG. 8 is a graph showing a relationship between a distance between needle tips of the discharge electrodes and an ion current.

FIG. 8 is a graph showing a relationship between distance L between the needle tips of discharge electrodes 40 and an ion current. The horizontal axis shown in FIG. 8 indicates distance L between first needle-like electrode 41 and third needle-like electrode 43 (or distance L between second needle-like electrode 42 and fourth needle-like electrode 44) (unit: centimeter). The vertical axis shown in FIG. 8 indicates the magnitude of the ion current generated by discharge electrodes 40. The ion current is measured on the downstream side with respect to discharge electrodes 40 in the direction of the air flow that conveys the ions generated by discharge electrodes 40. The graph in FIG. 8 shows a result of applicant's study of an influence of distance L on an amount of ions generated by discharge. The broken line shown in FIG. 8 indicates the magnitude of the ion current measured similarly by using a conventional ion generation apparatus.

As shown in FIG. 8, in order to generate a larger amount of ions than a conventional amount by using ion generation apparatus 26 according to the first embodiment, it is necessary to set distance L to be 5 cm or longer. In order to obtain an effect of reliably increasing the amount of generated ions as compared with the conventional ion generation apparatus, it is desirable to set distance L to be 10 cm or longer. On the other hand, when distance L exceeds a certain degree, the ion current decreases. With consideration also given to the fact that the apparatus can be reduced in size as distance L becomes shorter, it is desirable to set distance L to be within a range of 18 cm or shorter.

Similarly to distance L, the applicant studied optimum ranges of interval D1 between first needle-like electrode 41 and second needle-like electrode 42 as well as interval D2 between third needle-like electrode 43 and fourth needle-like electrode 44. As a result of the applicant's study, it is desirable to set intervals D1 and D2 to be within a range of 3.5 cm to 18 cm.

(Second Embodiment)

Figure 9:
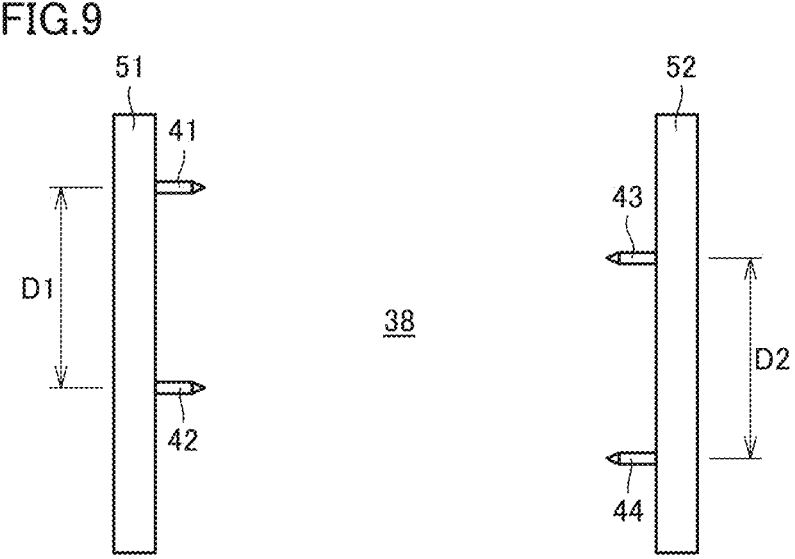
FIG. 9 is a schematic view showing arrangement of discharge electrodes of an ion generation apparatus according to a second embodiment.

FIG. 9 is a schematic view showing arrangement of discharge electrodes 40 of ion generation apparatus 26 according to a second embodiment. The arrangement of first to fourth needle-like electrodes 41 to 44 is not limited to the example shown in FIG. 7. FIG. 9 shows a first modification of the arrangement of discharge electrodes 40. For example, as shown in FIG. 9, interval D1 between first needle-like electrode 41 and second needle-like electrode 42 as well as interval D2 between third needle-like electrode 43 and fourth needle-like electrode 44 are similar to those of the arrangement shown in FIG. 7. However, first and second needle-like electrodes 41 and 42 may be arranged at positions displaced from those of third and fourth needle-like electrodes 43 and 44.

As shown in FIG. 9, the needle tip of first needle-like electrode 41 needs not to face the needle tip of third needle-like electrode 43, and the needle tip of second needle-like electrode 42 needs not to face the needle tip of fourth needle-like electrode 44. As long as the needle tips of first to fourth needle-like electrodes 41 to 44 protrude into space 38 and third and fourth needle-like electrodes 43 and 44 are arranged to face first and second needle-like electrodes 41 and 42 on the whole, the effect of increasing the amount of generated ions can be similarly obtained.

(Third Embodiment)

Figure 10:
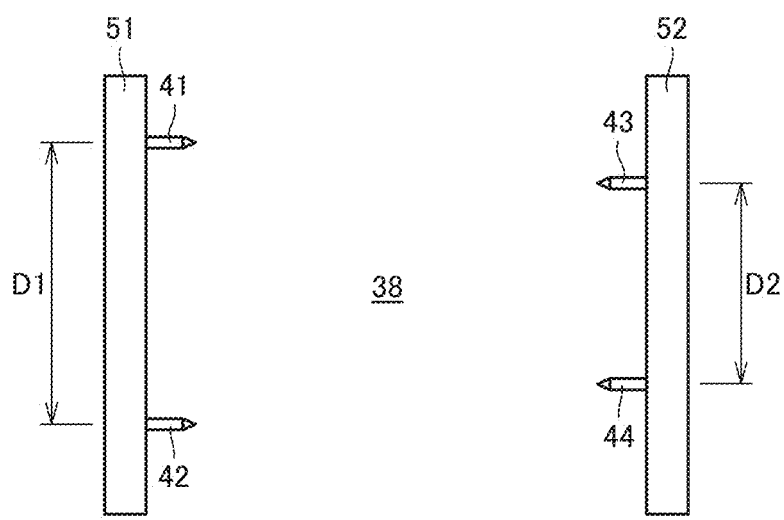
FIG. 10 is a schematic view showing arrangement of discharge electrodes of an ion generation apparatus according to a third embodiment.

FIG. 10 is a schematic view showing arrangement of discharge electrodes 40 of ion generation apparatus 26 according to a third embodiment. FIG. 10 shows a second modification of the arrangement of discharge electrodes 40. As shown in FIG. 10, interval D1 between first needle-like electrode 41 and second needle-like electrode 42 may be different from interval D2 between third needle-like electrode 43 and fourth needle-like electrode 44.

In the case of the arrangement shown in FIG. 10 in which intervals D1 and D2 are different from each other, it is desirable to make interval D1 larger than interval D2. In ion generation apparatus 26, induction electrode 45 is arranged between first needle-like electrode 41 and second needle-like electrode 42. Therefore, if interval D1 is made relatively larger, each of first and second needle-like electrodes 41 and 42 can be arranged at a position that is more distant from induction electrode 45, and thus, the amount of generated ions can be further increased.

Figure 11:
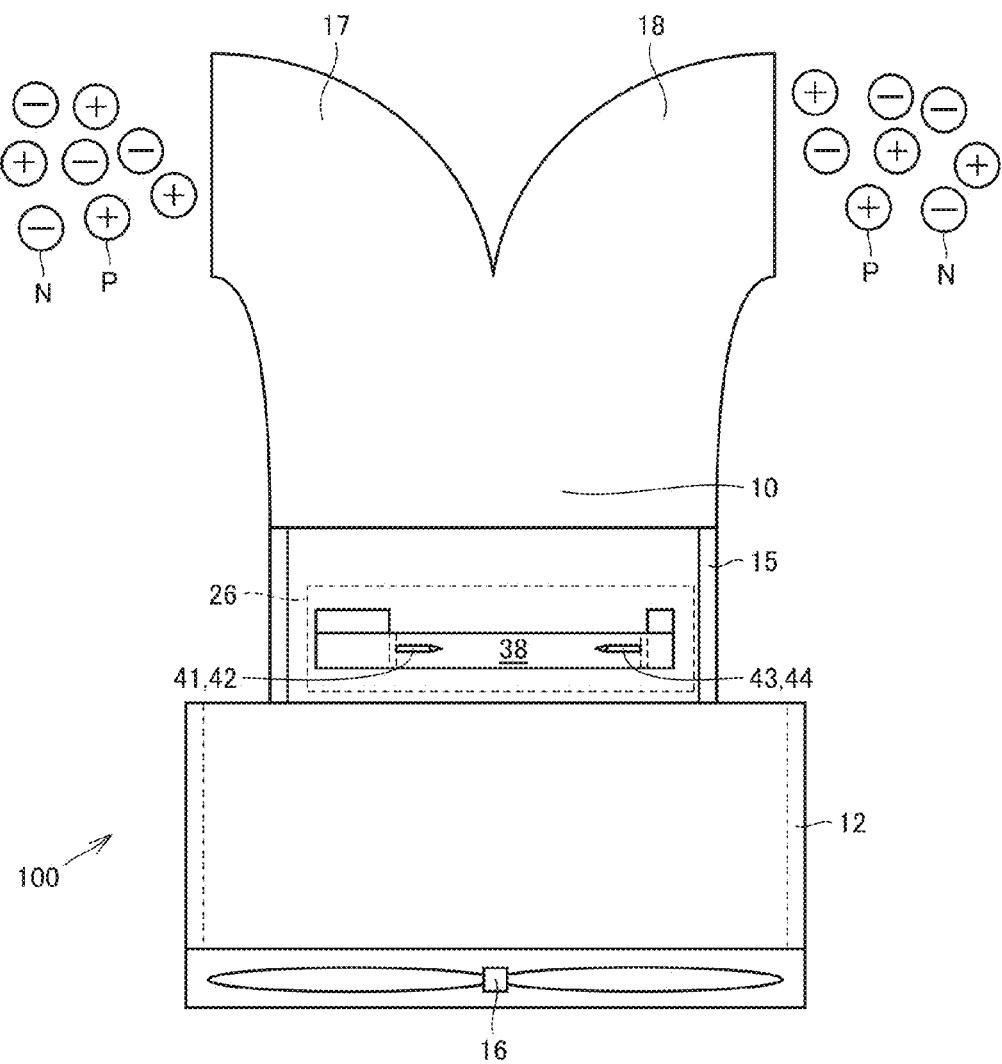
FIG. 11 is a side view showing a schematic configuration of electric equipment including the ion generation apparatus according to any one of the first to third embodiments.

FIG. 11 is a side view showing a schematic configuration of electric equipment 100 including ion generation apparatus 26 according to any one of the first to third embodiments. Electric equipment 100 may be, for example, an ion generator, an air conditioner, a dehumidifier, a humidifier, an air cleaner, a fan heater, or other equipment. Electric equipment 100 is equipment suitably used to condition the air in a room of a house, in a room of a building, in a room of a hospital, in a vehicle interior of an automobile, in a plane, in a ship, or the like.

As shown in FIG. 11, electric equipment 100 includes ion generation apparatus 26 described above, an air blower 16, and ducts 12, 15, 17, and 18. Ducts 12, 15, 17, and 18 are hollow, and interior spaces of ducts 12, 15, 17, and 18 communicate with one another to form an air flow path 10 through which the air flows. Air blower 16 is provided in an opening of duct 12 and forms an air flow in air flow path 10. Air blower 16 may be a sirocco fan, a cross flow fan or other fan.

Ion generation apparatus 26 is arranged inside duct 15. Space 38 defined by outer case 31 of ion generation apparatus 26 forms a part of air flow path 10. Space 38 communicates with a part of air flow path 10 formed by duct 15. Air blower 16 blows a gas into space 38 included in air flow path 10. The air flowing through air flow path 10 in duct 15 in FIG. 11 is flown through space 38. The air flowing through space 38 is flown in the upward direction in FIG. 11. Since the air flows through space 38, the ions generated by discharge electrode 40 are conveyed by the air flow, and are emitted from an outlet to the indoor space through air flow path 10. Electric equipment 100 is provided such that a structure blocking the air flow to first to fourth needle-like electrodes 41 to 44 is not arranged upwind and downwind of first to fourth needle-like electrodes 41 to 44 protruding into space 38.

On the downstream side of the air flow with respect to duct 15 that houses ion generation apparatus 26, air flow path 10 branches off into two paths. On the downstream side of the gas flow with respect to first to fourth needle-like electrodes 41 to 44, air flow path 10 branches off into two paths. Air flow path 10 has a pair of bifurcated ducts, i.e., ducts 17 and 18.

Duct 17 which is one of the bifurcated ducts is provided on an extension of first needle-like electrode 41 and second needle-like electrode 42 in the direction of the air flow in air flow path 10. Positive ions P and negative ions N generated by first needle-like electrode 41 and second needle-like electrode 42 are emitted from an outlet where duct 17 is open to the outside. Duct 18 which is the other of the bifurcated ducts is provided on an extension of third needle-like electrode 43 and fourth needle-like electrode 44 in the direction of the air flow in air flow path 10. Positive ions P and negative ions N generated by third needle-like electrode 43 and fourth needle-like electrode 44 are emitted from an outlet where duct 18 is open to the outside.

As described above, comparing interval D1, which is the distance between the needle tips of first and second needle-like electrodes 41 and 42, and distance L, which is the distance between the needle tips of first and third needle-like electrodes 41 and 43, distance L is longer. Air flow path 10 has the bifurcated ducts bifurcated in the direction of distance L (in the horizontal direction in FIG. 11) which is the longer one of interval D1 and distance L. The bifurcated ducts cause the air flow to branch off in the direction of distance L (in the horizontal direction in FIG. 11) which is the longer one of interval D1 and distance L.

Ion generation apparatus 26 may be configured to be integrally incorporated into electric equipment 100. Alternatively, ion generation apparatus 26 may be provided to be removable from electric equipment 100. In this case, ion generation apparatus 26 can be configured to be replaceable, which facilitates maintenance of electric equipment 100.

Figure 22:
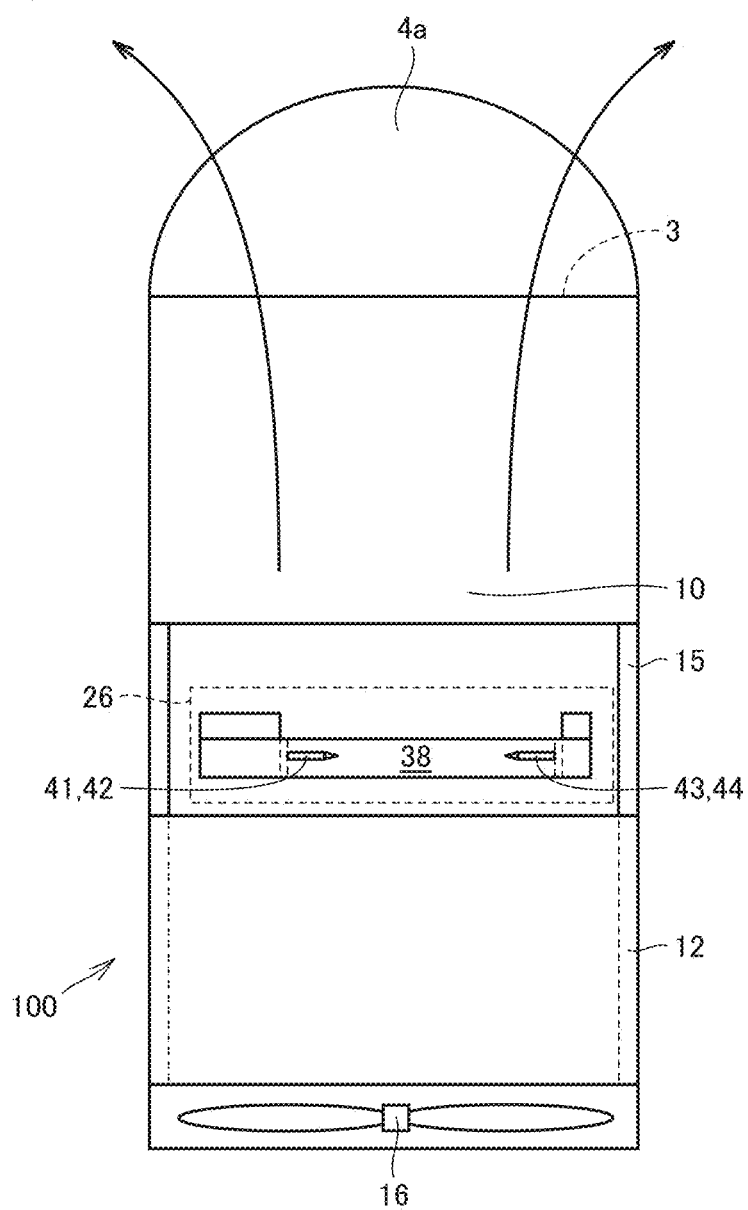
FIG. 22 is a side view showing a schematic configuration of electric equipment according to a second example.
Figure 23:
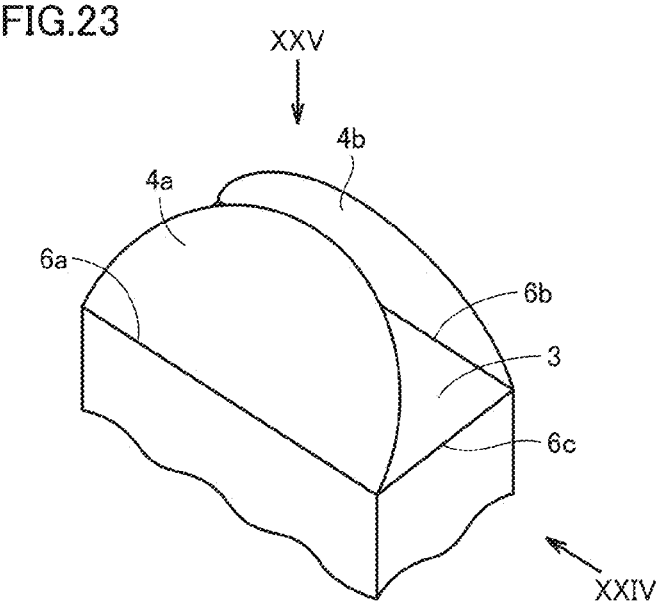
FIG. 23 is a perspective view showing a vicinity of an outlet of the electric equipment according to the second example.
Figure 24:
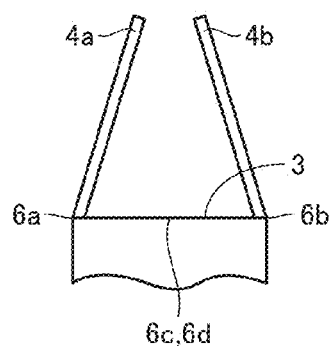
FIG. 24 is a side view showing the vicinity of the outlet of the electric equipment according to the second example.
Figure 25:
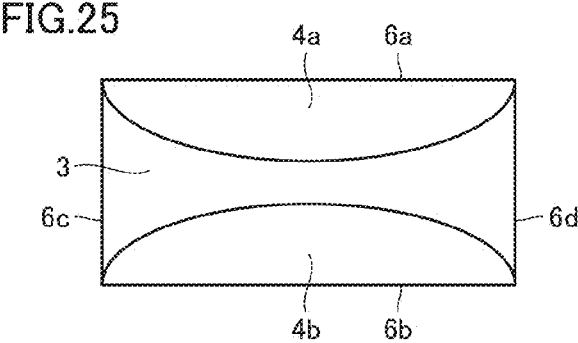
FIG. 25 is a schematic view of the electric equipment according to the second example viewed from the outlet side.
Figure 26:
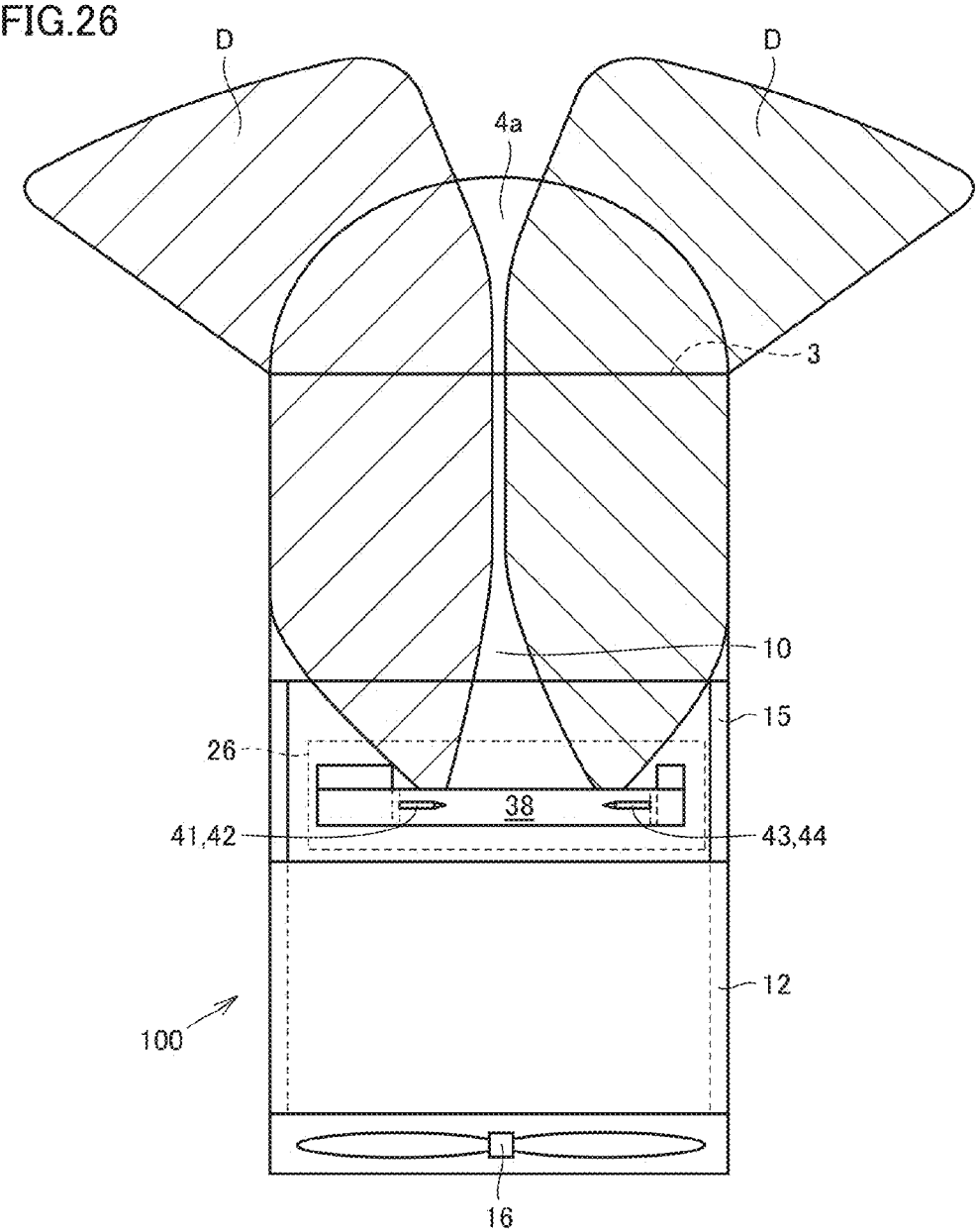
FIG. 26 is a schematic view showing an ion distribution in an air flow path of the electric equipment according to the second example.

FIG. 22 is a side view showing a schematic configuration of electric equipment according to a second example. FIG. 23 is a perspective view showing a vicinity of an outlet 3 of the electric equipment according to the second example. FIG. 24 is a side view showing the vicinity of outlet 3 of the electric equipment according to the second example. FIG. 25 is a schematic view of the electric equipment according to the second example viewed from the outlet 3 side. FIG. 26 is a schematic view showing an ion distribution in air flow path 10 of the electric equipment according to the second example. FIG. 24 illustrates the vicinity of outlet 3 viewed from the direction of an arrow XXIV shown in FIG. 23, and FIG. 25 illustrates the vicinity of outlet 3 viewed from the direction of an arrow XXV shown in FIG. 23. The electric equipment according to the second example will be described with reference to FIGS. 22 to 25.

Similarly to electric equipment 100 described with reference to FIG. 11, the electric equipment according to the second example includes ion generation apparatus 26, air blower 16 and ducts 12 and 15. Outlet 3 for blowing out the air from air flow path 10 is provided at a tip of air flow path 10 through which the air flows. Outlet 3 is formed to have a rectangular shape and has four sides 6a, 6b, 6c, and 6d. Two sides 6a and 6b face each other and extend in parallel. Two sides 6c and 6d face each other and extend in parallel. Two sides 6a and 6b and two sides 6c and 6d extend to be orthogonal to each other.

Outlet 3 is provided with adjustment plates 4a and 4b. Each of adjustment plates 4a and 4b extends from two sides 6a and 6b toward downstream of the gas flow. Adjustment plates 4a and 4b are arranged to be inclined such that a gap therebetween becomes narrower toward downstream of the gas flow. A width of adjustment plates 4a and 4b becomes narrower toward downstream of the gas flow, as compared with a width of portions of adjustment plates 4a and 4b that are in contact with outlet 3.

Each of adjustment plates 4a and 4b is formed to have a semicircular shape. The shape of each of adjustment plates 4a and 4b may be a semi-elliptical shape or a semi-polygonal shape. The semicircular shape includes not only an exact semicircular shape obtained by cutting a precise circle in half, but also a shape similar to the exact semicircular shape. The same is also applied to the semi-elliptical shape and the semi-polygonal shape. The semi-polygonal shape includes not only a shape obtained by cutting a precise polygonal shape in half, but also a shape obtained by cutting a polygonal shape other than the precise polygonal shape in half.

Each of adjustment plates 4a and 4b may be provided as a movable plate that is relatively movable with respect to outlet 3. Each of adjustment plates 4a and 4b may be provided to be relatively pivotable or slidable with respect to sides 6a and 6b of outlet 3. By relatively moving adjustment plates 4a and 4b with respect to outlet 3, an interval between adjustment plate 4a and adjustment plate 4b can be changed and an opening area of the flow path of the air blown out from outlet 3 can be changed. As a result, a state of the air blown out from outlet 3 can be freely adjusted.

Adjustment plates 4a and 4b may be inclined symmetrically with respect to outlet 3 of air flow path 10, or may be inclined at different angles. Alternatively, only one of two adjustment plates 4a and 4b may be inclined with respect to outlet 3 and the other may extend straight without being inclined.

In the electric equipment according to the second example shown in FIGS. 22 to 26, adjustment plates 4a and 4b extend from two sides 6a and 6b of outlet 3 that face each other, respectively. Adjustment plates 4a and 4b are arranged to be inclined such that the interval therebetween becomes narrower toward downstream of the gas flow, and the width of adjustment plates 4a and 4b becomes narrower toward downstream of the gas flow, as compared with the width of the portions of adjustment plates 4a and 4b that are in contact with outlet 3. As shown by an arrow in FIG. 22, the air blown out from outlet 3 branches off and flows. Therefore, as shown by an ion distribution D hatched in FIG. 26, the ions generated by first to fourth needle-like electrodes 41 to 44 are emitted over a wide range.

As described above, comparing interval D1, which is the distance between the needle tips of first and second needle-like electrodes 41 and 42, and distance L, which is the distance between the needle tips of first and third needle-like electrodes 41 and 43, distance L is longer. Adjustment plates 4a and 4b causes the air flow to branch off in the direction of distance L (in the horizontal direction in FIGS. 22 and 26) which is the longer one of interval D1 and distance L.

Figure 27:
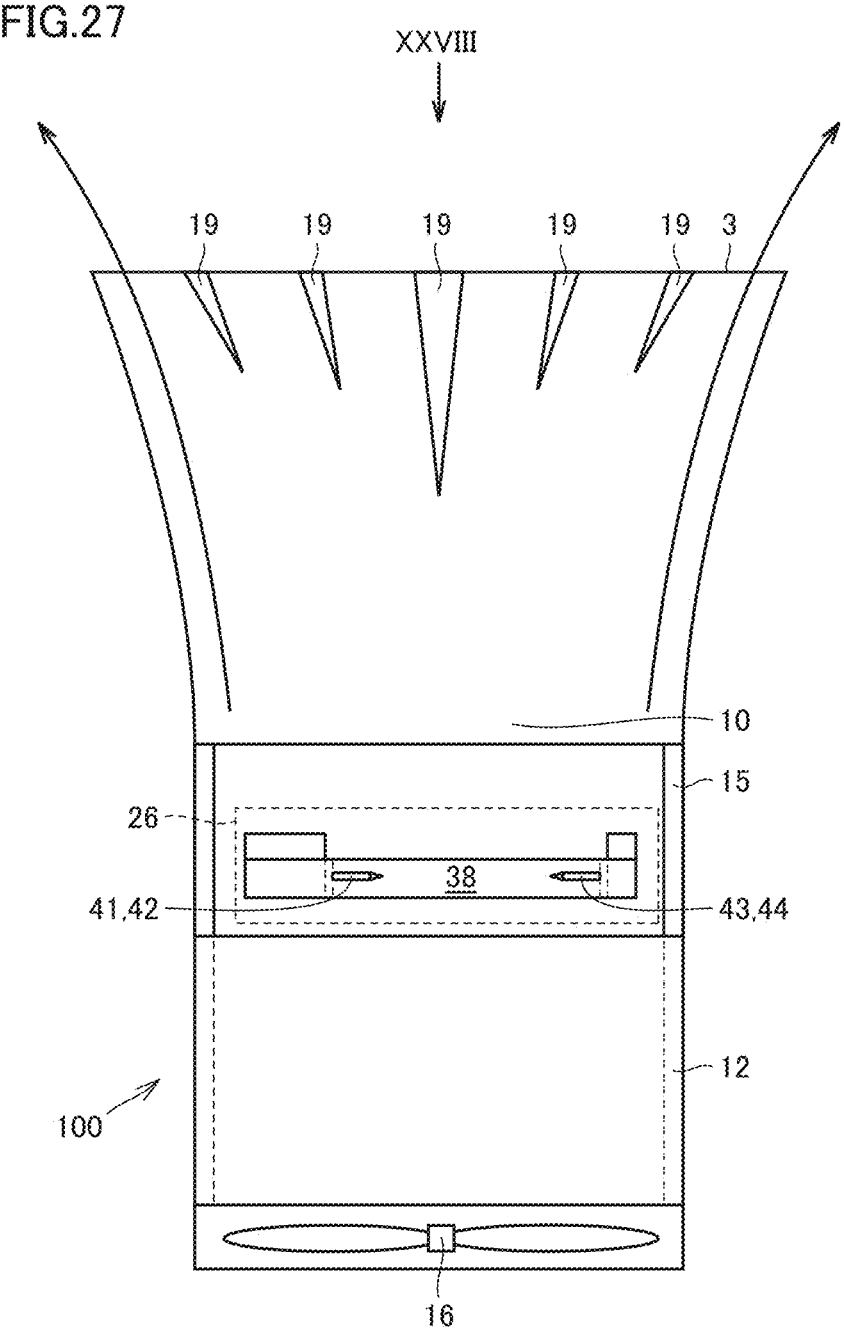
FIG. 27 is a side view showing a schematic configuration of electric equipment according to a third example.
Figure 28:
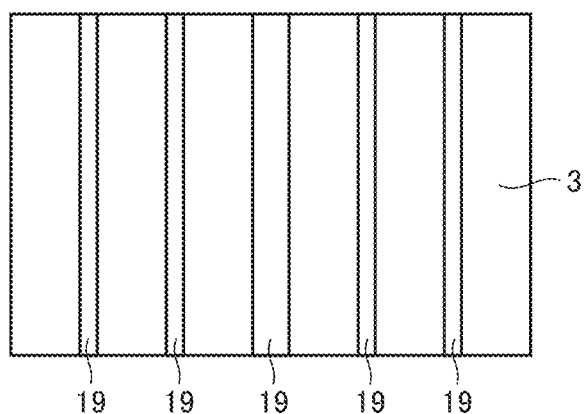
FIG. 28 is a schematic view of the electric equipment according to the third example viewed from the outlet side.
Figure 29:
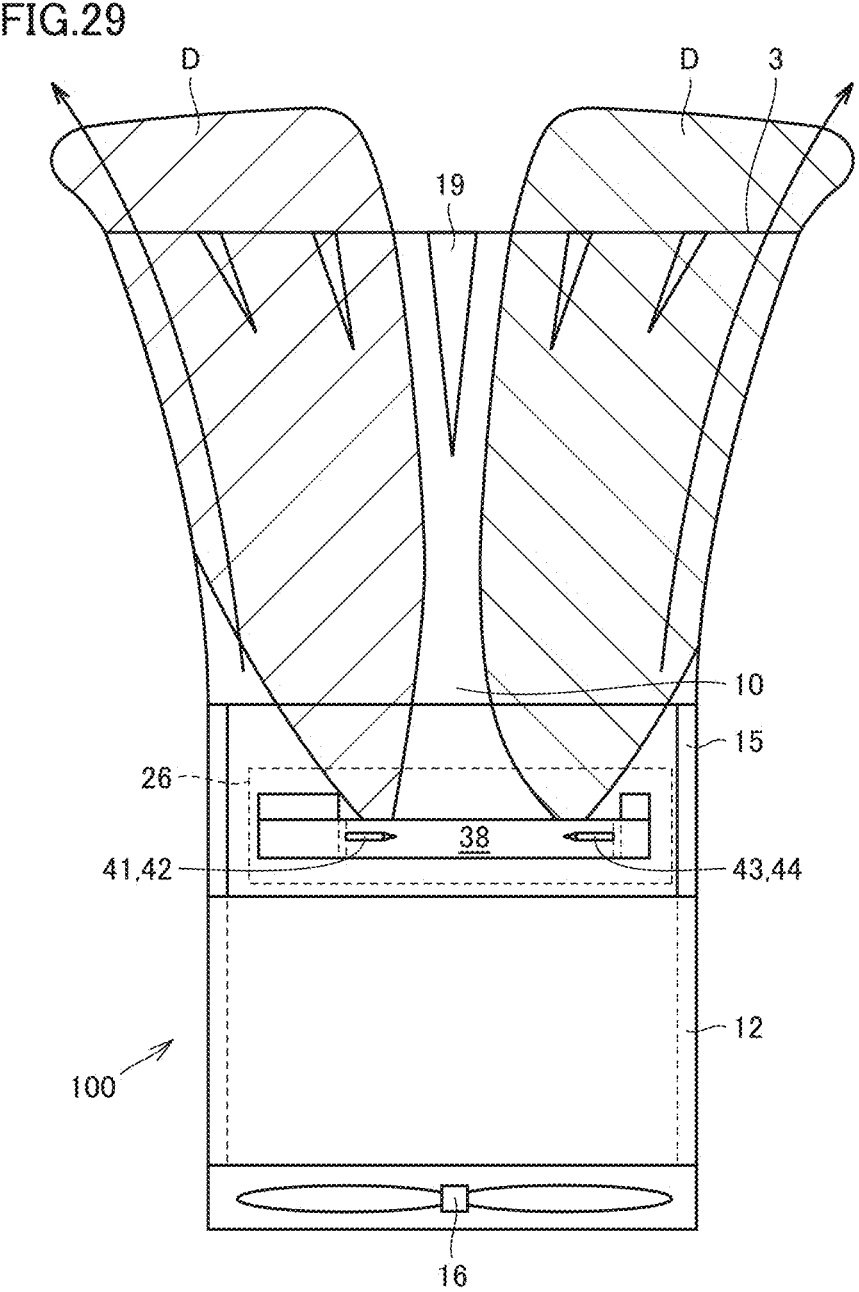
FIG. 29 is a schematic view showing an ion distribution in an air flow path of the electric equipment according to the third example.

FIG. 27 is a side view showing a schematic configuration of electric equipment according to a third example. FIG. 28 is a schematic view of the electric equipment according to the third example viewed from the outlet 3 side. FIG. 29 is a schematic view showing an ion distribution in air flow path 10 of the electric equipment according to the third example. FIG. 28 illustrates outlet 3 viewed from the direction of an arrow XXVIII shown in FIG. 27. The electric equipment according to the third example will be described with reference to FIGS. 27 to 29.

Similarly to electric equipment 100 described with reference to FIG. 11, the electric equipment according to the third example includes ion generation apparatus 26, air blower 16 and ducts 12 and 15. Outlet 3 for blowing out the air from air flow path 10 is provided at a tip of air flow path 10 through which the air flows. A plurality of flow path dividing members 19 are arranged in air flow path 10 downstream of the gas flow with respect to first to fourth needle-like electrodes 41 to 44. Flow path dividing members 19 extend along a direction of extension of air flow path 10. Flow path dividing members 19 are arranged to divide an interior space of air flow path 10 into a plurality of small spaces.

The air blown by air blower 16 flows through air flow path 10 along the direction of extension of flow path dividing members 19. Flow path dividing members 19 extend from the inside of air flow path 10 to outlet 3, and has a function of orienting the air flowing through air flow path 10 and blown out from outlet 3. The air is guided by flow path dividing members 19, and thus, the air blown out from outlet 3 branches off and flows as shown by an arrow in FIG. 27. As a result, the ions generated by first to fourth needle-like electrodes 41 to 44 are emitted over a wide range as shown by ion distribution D hatched in FIG. 26.

As described above, comparing interval D1, which is the distance between the needle tips of first and second needle-like electrodes 41 and 42, and distance L, which is the distance between the needle tips of first and third needle-like electrodes 41 and 43, distance L is longer. Flow path dividing members 19 cause the air flow to branch off in the direction of distance L (in the horizontal direction in FIGS. 22 and 26) which is the longer one of interval D1 and distance L. Flow path dividing members 19 extend in the direction of interval D1 (in the vertical direction in FIG. 28) which is the shorter one of interval D1 and distance L.

(Fourth Embodiment)

Figure 12:
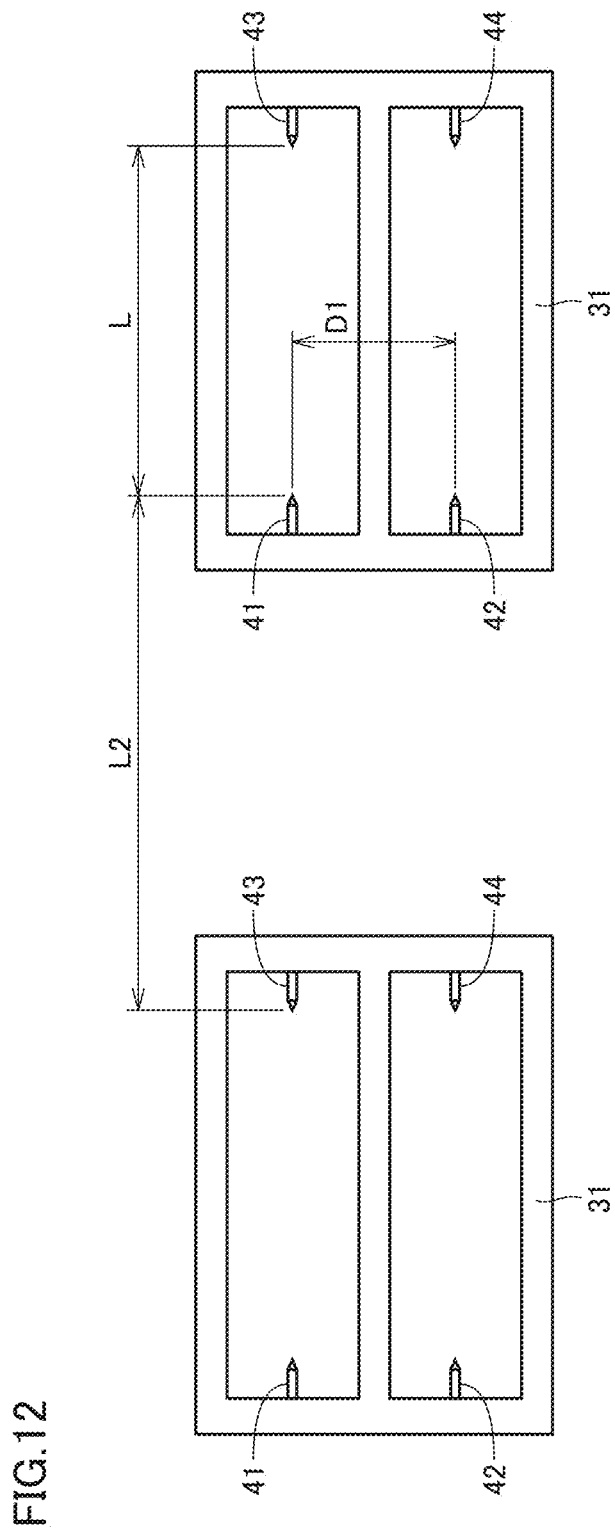
FIG. 12 is a schematic view showing arrangement of discharge electrodes of an ion generation apparatus according to a fourth embodiment.

FIG. 12 is a schematic view showing arrangement of discharge electrodes 40 of ion generation apparatus 26 according to a fourth embodiment. FIG. 12 shows a third modification of the arrangement of discharge electrodes 40. Electric equipment 100 shown in FIG. 11 is provided with one ion generation apparatus 26. However, electric equipment 100 is not limited to this example and a plurality of ion generation apparatuses 26 may be provided. For example, as shown in FIG. 12, electric equipment 100 such as an ion generator may be configured to include a plurality of sets (two sets in the example of FIG. 12) of first to fourth needle-like electrodes 41 to 44 supported by outer case 31 and integrated into one unit.

In this case, a distance between the needle tips of discharge electrodes 40 included in the two adjacent units, i.e., a distance L2 between the needle tip of third needle-like electrode 43 on the left side and the needle tip of first needle-like electrode 41 on the right side shown in FIG. 12, may be made larger than distance L described above. For example, distance L2 may be set to be one-and-a-half times larger than distance L.

(Fifth Embodiment)

Figure 13:
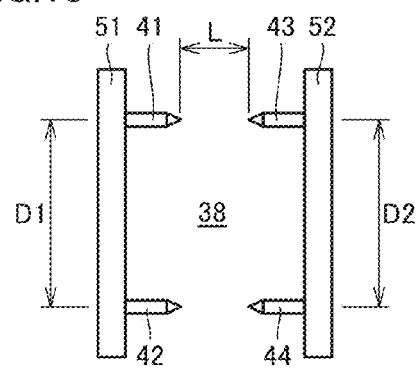
FIG. 13 is a schematic view showing arrangement of discharge electrodes of an ion generation apparatus according to a fifth embodiment.

FIG. 13 is a schematic view showing arrangement of discharge electrodes 40 of ion generation apparatus 26 according to a fifth embodiment. FIG. 13 shows a fourth modification of the arrangement of discharge electrodes 40. The foregoing description has been given to the example in which interval D1 between the needle tips of first and second needle-like electrodes 41 and 42 is smaller than distance L between the needle tips of first and third needle-like electrodes 41 and 43. However, first to fourth needle-like electrodes 41 to 44 are not limited to this example. As shown in FIG. 13, first to fourth needle-like electrodes 41 to 44 may be arranged such that interval D1 is larger than distance L.

In this case, if air flow path 10 is configured to have the bifurcated ducts, the gas may branch off in the direction of interval D1 which is the longer one of interval D1 and distance L. In the case of the arrangement shown in FIG. 13, the duct may be bifurcated in the vertical direction in the figure, such that one of the bifurcated ducts is supplied with the positive ions generated by first needle-like electrode 41 and the negative ions generated by the third needle-like electrode, and the other of the bifurcated ducts is supplied with the negative ions generated by the second needle-like electrode and the positive ions generated by fourth needle-like electrode 44.

Alternatively, adjustment plates extending from two sides of an outlet extending in the vertical direction in FIG. 13 may be provided, or a flow path dividing member extending in the horizontal direction in FIG. 13 may be provided.

(Sixth Embodiment)

Figure 14:
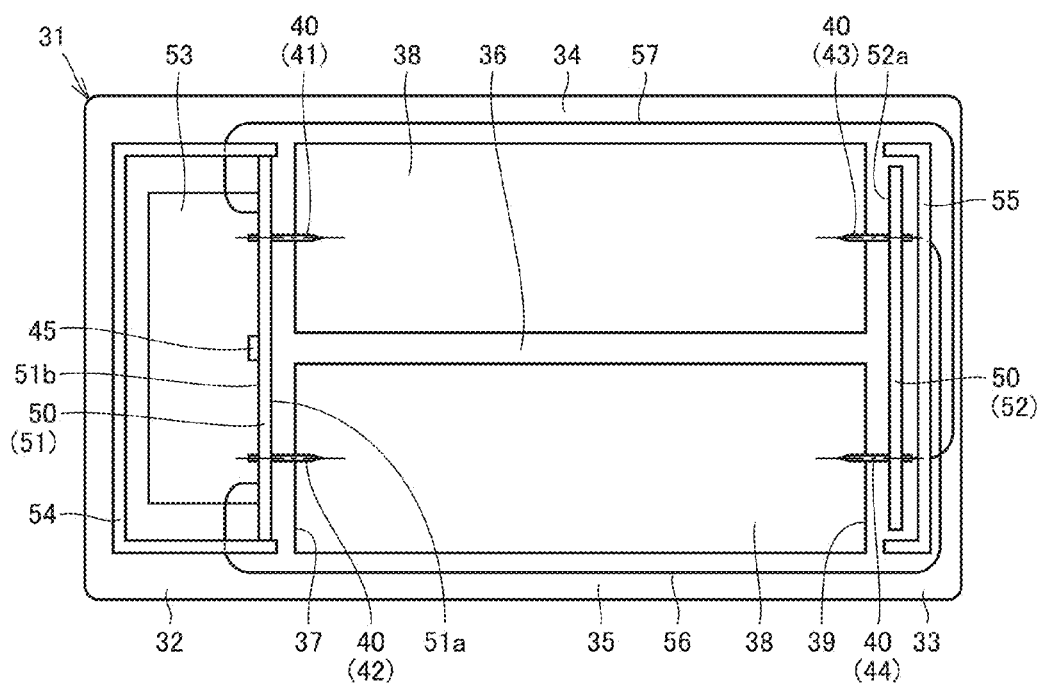
FIG. 14 is a plan view showing an internal structure of an ion generation apparatus according to a sixth embodiment.

FIG. 14 is a plan view showing an internal structure of ion generation apparatus 26 according to a sixth embodiment. FIG. 14 shows the internal structure of ion generation apparatus 26 including induction electrode 45 arranged according to a modification. As compared with the configuration of ion generation apparatus 26 shown in FIG. 4, induction electrode 45 is provided on the other surface 51b side with respect to substrate 51 in the modification shown in FIG. 14. Induction electrode 45 is formed by a wiring pattern of high voltage generation circuit portion 53. In the case of forming induction electrode 45 by a printing pattern on substrate 51, the number of components can be reduced and the processing cost can be suppressed as compared with a configuration including pin-like induction electrode 45.

The configurations and the function and effect of ion generation apparatus 26 and electric equipment 100 according to the embodiments will be summarized as follows. Although the reference numerals are assigned to the configurations according to the embodiments, this is one example.

Ion generation apparatus 26 according to one aspect of the present embodiment includes: discharge electrodes 40 including first to fourth needle-like electrodes 41 to 44, each of which is arranged such that a direction of extension thereof is parallel and each of which generates ions by discharge; and air flow path 10 through which a gas for conveying the ions generated by discharge electrodes 40 flows. The needle tips of first needle-like electrode 41 and second needle-like electrode 42 protrude from first wall surface 37 that forms air flow path 10, are spaced apart from each other by interval D1 as the first interval, and are arranged in line in space 38 included in air flow path 10. The needle tips of third needle-like electrode 43 and fourth needle-like electrode 44 protrude from second wall surface 39 that forms air flow path 10 and faces first wall surface 37, are spaced apart from each other by interval D2 as the second interval, and are arranged in line in space 38 included in air flow path 10. First needle-like electrode 41 and fourth needle-like electrode 44 generate positive ions P, and second needle-like electrode 42 and third needle-like electrode 43 generate negative ions N.

With this, the ions generated by first to fourth needle-like electrodes 41 to 44 arranged in parallel in air flow path 10 can be spread over a wide area and it is possible to cause a high concentration of positive and negative ions to be present over a wide range.

Preferably, the needle tip of first needle-like electrode 41 and the needle tip of third needle-like electrode 43 face each other. As a result, first needle-like electrode 41 and third needle-like electrode 43 are arranged in line on the same straight line, and thus, ion generation apparatus 26 can be reduced in size.

Preferably, distance L between the needle tip of first needle-like electrode 41 and the needle tip of third needle-like electrode 43 is larger than interval D1 and larger than interval D2. With this, first needle-like electrode 41 and third needle-like electrode 43 that generate the ions of opposite polarities can be spaced apart from each other, and thus, the positive ions and the negative ions can be spread over a wider range. In addition, it is possible to suppress a reduction in ion concentration caused by neutralization of the generated positive and negative ions, recovery of the ions at the opposite polarity electrodes, or the like, and thus, a higher concentration of ions can be generated.

Preferably, the needle tip of second needle-like electrode 42 and the needle tip of fourth needle-like electrode 44 face each other. As a result, second needle-like electrode 42 and fourth needle-like electrode 44 are arranged in line on the same straight line, and thus, ion generation apparatus 26 can be reduced in size.

Preferably, distance L between the needle tip of second needle-like electrode 42 and the needle tip of fourth needle-like electrode 44 is larger than first interval D1 and larger than second interval D2. With this, second needle-like electrode 42 and fourth needle-like electrode 44 that generate the ions of opposite polarities can be spaced apart from each other, and thus, the positive ions and the negative ions can be spread over a wider range. In addition, it is possible to suppress a reduction in ion concentration caused by neutralization of the generated positive and negative ions, and thus, a higher concentration of ions can be generated.

Preferably, ion generation apparatus 26 further includes: base member 50 having discharge electrodes 40 mounted thereon; and outer case 31 as a casing that houses base member 50. A part of outer surface 31s of outer case 31 forms first wall surface 37 and second wall surface 39. Outer case 31 is provided such that space 38 forming a part of air flow path 10 is formed between first wall surface 37 and second wall surface 39. With this, first wall surface 37 and second wall surface 39 facing each other form an inner wall surface of space 38 provided as a part of the configuration of air flow path 10, and discharge electrodes 40 generate a high concentration of ions both on the first wall surface 37 side and on the second wall surface 39 side. Therefore, the ions generated by the discharge electrodes can be reliably spread over a wide area.

Preferably, space 38 that forms a part of air flow path 10 is formed to pass through outer case 31. In this case, the ions are generated by discharge at the needle tips of first to fourth needle-like electrodes 41 to 44. Since the needle tips of first to fourth needle-like electrodes 41 to 44 protrude into space 38, the ions are generated in space 38. Since space 38 is formed to have a shape passing through outer case 31 and the air flow flowing through space 38 is formed, the ions generated by first to fourth needle-like electrodes 41 to 44 can be conveyed efficiently. Therefore, the generated ions can be spread at an early stage and it is possible to suppress a reduction in ion concentration caused by neutralization of the positive and negative ions.

Preferably, base member 50 includes, as separate base members, substrate 51 which is the first base member, and substrate 52 which is the second base member. First needle-like electrode 41 and second needle-like electrode 42 are mounted on substrate 51, and third needle-like electrode 43 and fourth needle-like electrode 44 are mounted on substrate 52. With this, first needle-like electrode 41 and second needle-like electrode 42 can be arranged at a position away from third needle-like electrode 43 and fourth needle-like electrode 44, and thus, first to fourth needle-like electrodes 41 to 44 can be arranged such that a high concentration of ions are easily spread over a wide area.

Preferably, ion generation apparatus 26 includes: boosting transformer 91 having secondary winding 91b, one end of which is electrically connected to first to fourth needle-like electrodes 41 to 44, and generating the positive or negative high voltage applied to each of first to fourth needle-like electrodes 41 to 44; and induction electrode 45 electrically connected to the other end of secondary winding 91b of boosting transformer 91. With this, the high voltage can be applied to each of first to fourth needle-like electrodes 41 to 44 by using one boosting transformer 91, and thus, the number of the high voltage generation circuits can be minimized Therefore, the number of components can be reduced and the manufacturing cost of ion generation apparatus 26 can be suppressed. Furthermore, the power consumption of ion generation apparatus 26 can be reduced.

Preferably, induction electrode 45 is arranged between first needle-like electrode 41 and second needle-like electrode 42 and at a distance from both first needle-like electrode 41 and second needle-like electrode 42. With this, one induction electrode 45 can suffice for four discharge electrodes 40. The number of induction electrode 45 can be reduced depending on the number of the high voltage generation circuits, and thus, the efficiency of ion generation can be improved. In addition, since only one induction electrode 45 is arranged at a position away from first to fourth needle-like electrodes 41 to 44, it is possible to suppress a reduction in ion concentration caused by recovery, at induction electrode 45, of the ions generated by first to fourth needle-like electrodes 41 to 44.

By providing induction electrode 45 in between first needle-like electrode 41 and second needle-like electrode 42, induction electrode 45 can be arranged at a position that is most distant from both first and second needle-like electrodes 41 and 42. Since induction electrode 45 is housed in outer case 31 made of an insulating resin material, an amount of ions recovered and dissipated at induction electrode 45 can be further reduced.

Third needle-like electrode 43 is arranged such that the needle tip thereof is directed to induction electrode 45. The ions generated by third needle-like electrode 43 are emitted from the needle tip of third needle-like electrode 43 toward induction electrode 45. The ions generated by first needle-like electrode 41 are emitted in the direction away from induction electrode 45. By making the distance between induction electrode 45 and third needle-like electrode 43 arranged such that the needle tip thereof is directed to induction electrode 45 larger than the distance between first needle-like electrode 41 and induction electrode 45, arrival of the ions generated by third needle-like electrode 43 at induction electrode 45 can be suppressed. The amount of ions recovered and dissipated at induction electrode 45 can be reduced, and thus, ion generation apparatus 26 can generate a higher concentration of ions.

Electric equipment according to one aspect of the present embodiment includes: ion generation apparatus 26 according to any one of the aforementioned aspects; and air blower 16 for blowing a gas into air flow path 10 of ion generation apparatus 26. According to electric equipment 100 configured as described above, the ions generated by first to fourth needle-like electrodes 41 to 44 arranged in parallel in air flow path 10 can be spread over a wide area and it is possible to cause a high concentration of positive and negative ions to be present over a wide range. In the case where electric equipment 100 is household electric equipment used in a room, a state of a higher concentration of positive and negative ions over a wide range in the room can be obtained.

Electric equipment 100 according to another aspect of the present embodiment includes: discharge electrodes 40 including first to fourth needle-like electrodes 41 to 44, each of which is arranged such that a direction of extension thereof is parallel and each of which generates ions by discharge; and air flow path 10 through which a gas for conveying the ions generated by discharge electrodes 40 flows. The needle tips of first needle-like electrode 41 and second needle-like electrode 42 protrude from first wall surface 37 that forms air flow path 10, are spaced apart from each other by interval D1 as the first interval, and are arranged in line in space 38 included in air flow path 10. The needle tips of third needle-like electrode 43 and fourth needle-like electrode 44 protrude from second wall surface 39 that forms air flow path 10 and faces first wall surface 37, are spaced apart from each other by interval D2 as the second interval, and are arranged in line in space 38 included in air flow path 10. First needle-like electrode 41 and fourth needle-like electrode 44 generate positive ions P, and second needle-like electrode 42 and third needle-like electrode 43 generate negative ions N. With this, the ions generated by first to fourth needle-like electrodes 41 to 44 arranged in parallel in air flow path 10 can be spread over a wide area and it is possible to cause a high concentration of positive and negative ions to be present over a wide range.

Electric equipment 100 which is an ion generation apparatus according to another aspect of the present embodiment includes: air flow path 10 through which a gas flows; first needle-like electrode 41 and second needle-like electrode 42 protruding into space 38 from first wall surface 37 that forms space 38 included in air flow path 10, arranged to extend in a direction orthogonal to a gas flowing direction in space 38, and generating ions by discharge; and third needle-like electrode 43 and fourth needle-like electrode 44 protruding into space 38 from second wall surface 39 that forms space 38 included in air flow path 10 and faces first wall surface 37, arranged to extend in the direction orthogonal to the gas flowing direction in space 38, and generating ions by discharge. First needle-like electrode 41 and second needle-like electrode 42 are arranged such that the needle tips thereof are spaced apart from each other by interval D1 as the first distance in the direction orthogonal to the gas flowing direction in space 38. First needle-like electrode 41 and third needle-like electrode 43 are arranged such that the needle tips thereof face each other and are spaced apart from each other by distance L as the second distance in the direction orthogonal to the gas flowing direction in space 38. On a downstream side of a gas flow with respect to first to fourth needle-like electrodes 41 to 44, air flow path 10 causes the gas flow to branch off in a direction of the longer one of interval D1 and distance L.

As shown in FIG. 11, on the downstream side of the gas flow with respect to first to fourth needle-like electrodes 41 to 44, air flow path 10 may have ducts 17 and 18 bifurcated in the direction of the longer one of interval D1 and distance L.

Alternatively, as shown in FIGS. 22 to 26, air flow path 10 may be provided with outlet 3 through which the gas is blown out from air flow path 10. Outlet 3 has sides 6a and 6b extending in the direction of the longer one of interval D1 and distance L, and facing each other. Sides 6a and 6b may be provided with a pair of adjustment plates 4a and 4b. Adjustment plates 4a and 4b are arranged to be inclined such that an interval therebetween becomes narrower toward downstream of the gas flow, and a width of adjustment plates 4a and 4b becomes narrower toward downstream of the gas flow, as compared with a width of portions of adjustment plates 4a and 4b that are in contact with outlet 3.

Alternatively, as shown in FIGS. 27 to 29, flow path dividing member 19 for dividing an internal space of air flow path 10 may be provided, and flow path dividing member 19 may extend in a direction of the shorter one of interval D1 and distance L.

With this, from the discharge electrodes facing each other and having a positional relationship of the longer distance, the positive and negative ions are independently blown into the outlet, and thus, extreme neutralization of the positive and negative ions can be suppressed. More specifically, the ions generated by first and second needle-like electrodes 41 and 42 are conveyed by one of the branched air flows and blown out from outlet 3. The ions generated by third and fourth needle-like electrodes 43 and 44 are conveyed by the other of the branched air flows and blown out from outlet 3. Therefore, the ions generated by first to fourth needle-like electrodes 41 to 44 can be spread over a wide area and it is possible to cause a high concentration of positive and negative ions to be present over a wide range.

Preferably, one of the two needle-like electrodes, e.g., first and second needle-like electrodes 41 and 42, that form the shorter one of interval D1 and distance L generates positive ions P, and the other generates negative ions N. With this, the positive ions and the negative ions generated by the two needle-like electrodes are flown into one of ducts 17 and 18, and the positive ions and the negative ions are mixed as the positive ions and the negative ions come closer to the outlet. Such a configuration that the positive ions and the negative ions are mixed in a region where the ion concentration is reduced to some extent in air flow path 10 downwind of discharge electrodes 40 allows the positive ions and the negative ions to be mixed with the air in a balanced manner. Since the air including a high concentration of positive and negative ions can be emitted from both of the pair of outlets, it is possible to cause a high concentration of positive and negative ions to be present over a wide range.

Preferably, first to fourth needle-like electrodes 41 to 44 are integrated into one unit. With this, the accuracy of positioning of first to fourth needle-like electrodes 41 to 44 can be improved, and further, handling of first to fourth needle-like electrodes 41 to 44 becomes easy.

Preferably, electric equipment 100 includes a plurality of sets of first to fourth needle-like electrodes 41 to 44 integrated into one unit. The plurality of units of first to fourth needle-like electrodes 41 to 44 are arranged side by side. With this, even when the outlets which are exits of ducts 17 and 18 have an elongated shape, the air including a high concentration of positive and negative ions can be emitted from both of the pair of outlets.

Preferably, electric equipment 100 further includes rib-like portion 36 serving as a partition plate for partitioning the two needle-like electrodes that form the shorter one of interval D1 and distance L. Rib-like portion 36 forms a part of outer case 31 and is made of an insulating resin material. With this, the two needle-like electrodes generating the ions of opposite polarities are spatially blocked by rib-like portion 36, and thus, it is possible to effectively suppress a reduction in ion concentration caused by neutralization of the positive and negative ions of opposite polarities.

EXAMPLE

Figure 15:
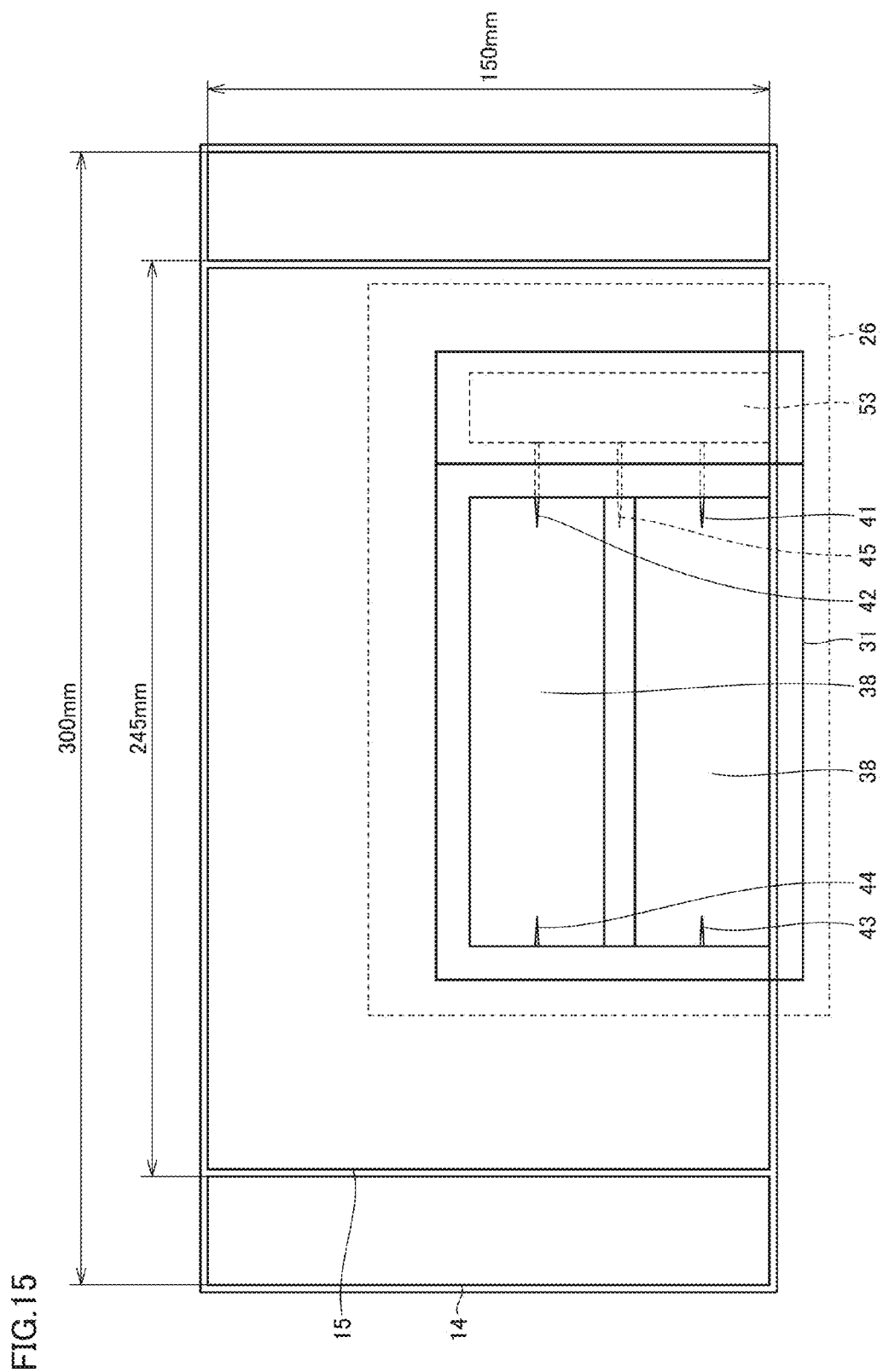
FIG. 15 is a schematic view showing a state in which an ion generation apparatus according to Example 1 is arranged in an air flow path.

Examples of the present invention will be described hereinafter. FIG. 15 is a schematic view showing a state in which ion generation apparatus 26 according to Example 1 is arranged in air flow path 10. As shown in FIG. 15, duct 15 for forming air flow path 10 was provided in a housing 14 corresponding to the casing of electric equipment 100, and ion generation apparatus 26 according to the first embodiment described with reference to FIGS. 1 to 5 was arranged in duct 15. As shown in FIG. 15, a dimension of housing 14 was set at a width of 300 mm and a height of 150 mm, and a dimension of duct 15 was set at a width of 245 mm and a height of 150 mm. The air was blown into this duct 15 by a not-shown cross flow fan such that a flow velocity at discharge electrodes 40 was 5 m/s.

Each of first to fourth needle-like electrodes 41 to 44 was provided such that the needle tip thereof protruded from outer case 31 by 9.5 mm Each of the distance between the needle tip of first needle-like electrode 41 and the needle tip of third needle-like electrode 43 as well as the distance between the needle tip of second needle-like electrode 42 and the needle tip of fourth needle-like electrode 44 was set at 101 mm Each of interval D1 between the needle tip of first needle-like electrode 41 and the needle tip of second needle-like electrode 42 as well as interval D2 between the needle tip of third needle-like electrode 43 and the needle tip of fourth needle-like electrode 44 was set at 42 mm.

Duct 15 was arranged such that the air flowed in the direction perpendicular to the drawing sheet of FIG. 15, and ion generation apparatus 26 was arranged, with outer case 31 standing in duct 15, such that the air flowing through duct 15 passed through space 38. As a result, first to fourth needle-like electrodes 41 to 44 were arranged to extend in the direction orthogonal to the direction of the air flow in duct 15. In order to bring conditions closer to those of an ion generation apparatus according to Comparative Example 1 described below, ion generation apparatus 26 according to Example 1 was arranged to be displaced in the height direction in duct 15. Specifically, ion generation apparatus 26 according to Example 1 was arranged such that an axis connecting first needle-like electrode 41 and third needle-like electrode 43 was located at a position of 18.5 mm from an inner wall of duct 15 on the bottom surface side.

Figure 16:
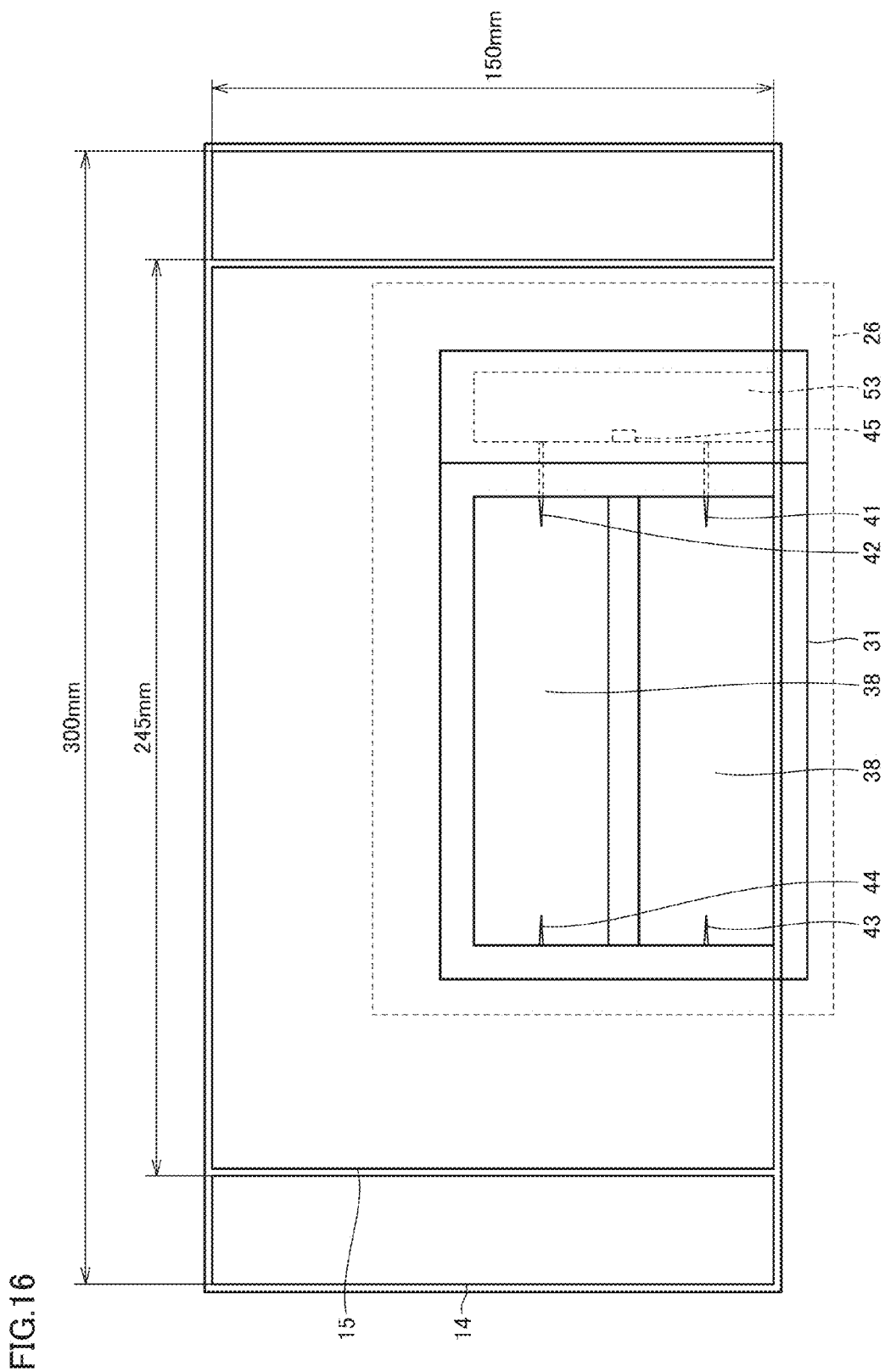
FIG. 16 is a schematic view showing a state in which an ion generation apparatus according to Example 2 is arranged in an air flow path.

FIG. 16 is a schematic view showing a state in which ion generation apparatus 26 according to Example 2 is arranged in air flow path 10. Ion generation apparatus 26 according to Example 2 had the configuration of ion generation apparatus 26 according to the sixth embodiment described with reference to FIG. 14, i.e., the configuration in which induction electrode 45 was provided in a wiring pattern manner in high voltage generation circuit portion 53. As shown in FIG. 16, ion generation apparatus 26 according to Example 2 was similarly arranged in duct 15 having the same shape as that of duct 15 in FIG. 15.

Figure 17:
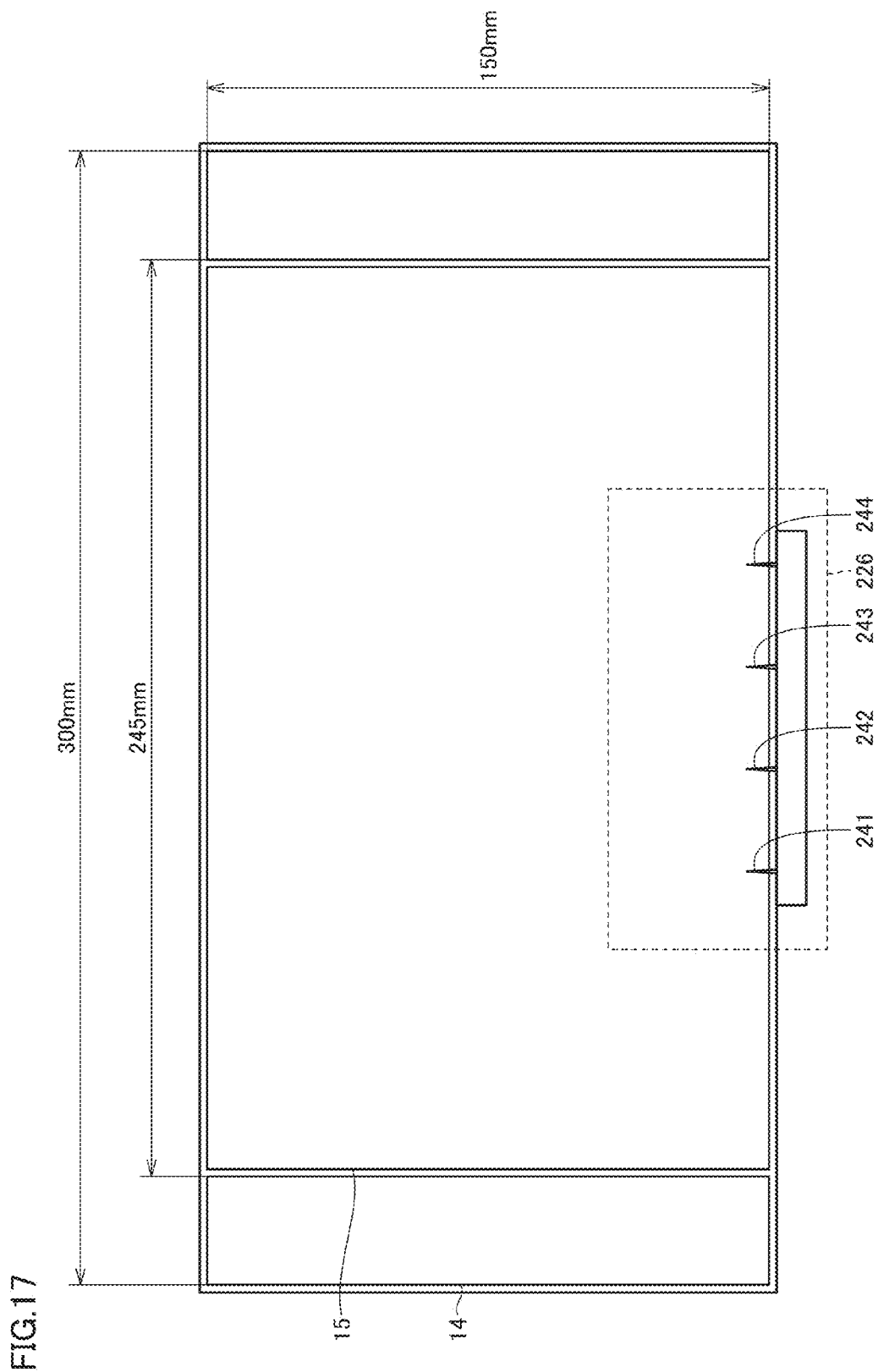
FIG. 17 is a schematic view showing a state in which an ion generation apparatus according to Comparative Example 1 is arranged in an air flow path.

FIG. 17 is a schematic view showing a state in which an ion generation apparatus 226 according to Comparative Example 1 is arranged in air flow path 10. Ion generation apparatus 226 according to Comparative Example 1 includes a first needle-like electrode 241, a second needle-like electrode 242, a third needle-like electrode 243, and a fourth needle-like electrode 244 that are discharge electrodes, and four annular induction electrodes that surround the respective discharge electrodes. A positive or negative high voltage is applied to each of first to fourth needle-like electrodes 241 to 244, and each of first to fourth needle-like electrodes 241 to 244 generates positive ions or negative ions.

Ion generation apparatus 226 according to Comparative Example 1 described above was arranged in duct 15 having the same shape as that of duct 15 in FIG. 15 and at a position on the bottom surface side in the height direction in duct 15. First to fourth needle-like electrodes 241 to 244 were provided such that the needle tips thereof protruded into duct 15 by 7 mm.

Figure 18:
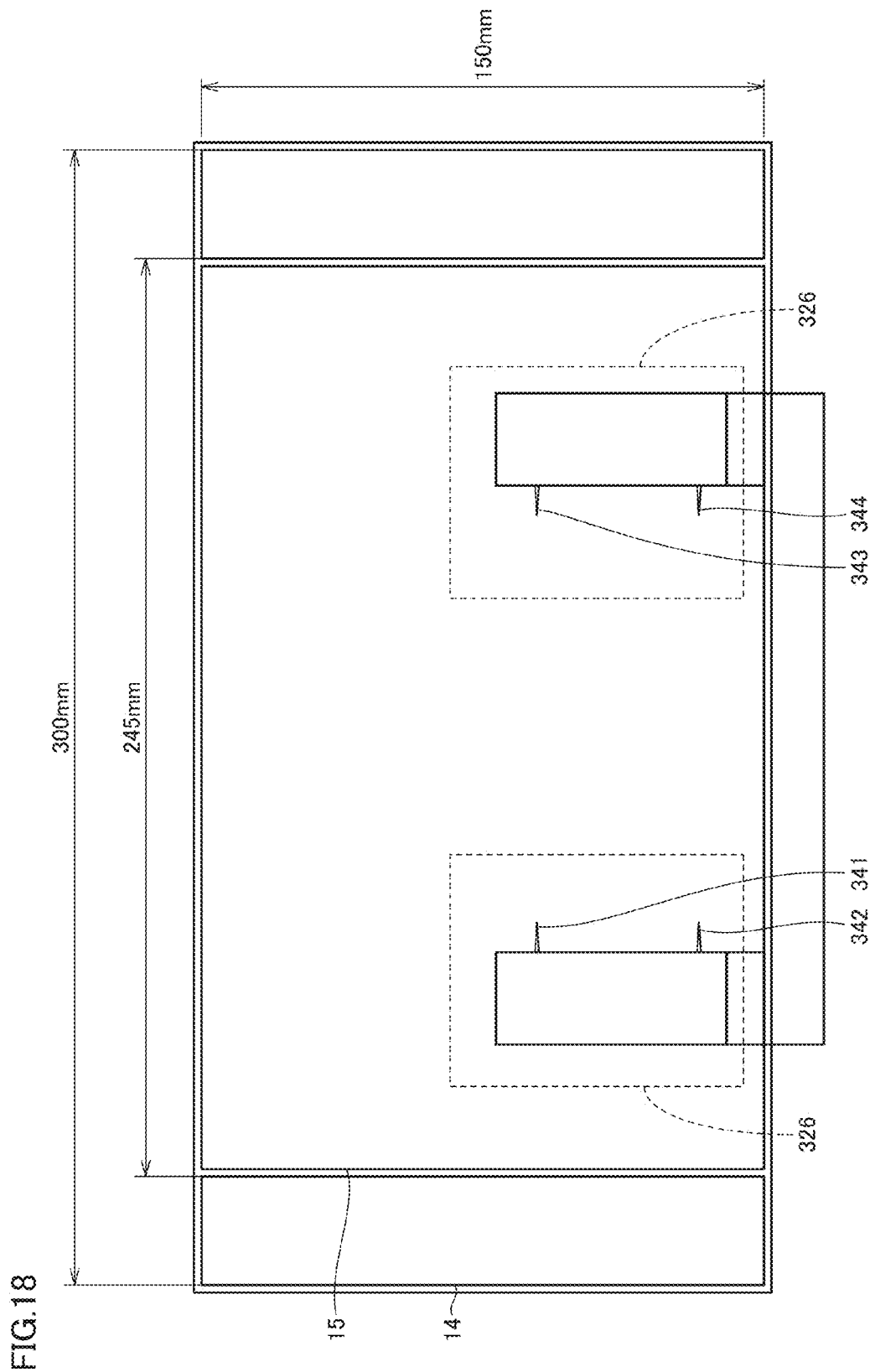
FIG. 18 is a schematic view showing a state in which an ion generation apparatus according to Comparative Example 2 is arranged in an air flow path.

FIG. 18 is a schematic view showing a state in which an ion generation apparatus 326 according to Comparative Example 2 is arranged in air flow path 10. In Comparative Example 2, two ion generation apparatuses 326 and 326 are provided, and one ion generation apparatus 326 includes a first needle-like electrode 341 and a second needle-like electrode 342 that are discharge electrodes of opposite polarities, and two annular induction electrodes that surround the respective discharge electrodes. The other ion generation apparatus 326 includes a third needle-like electrode 343 and a fourth needle-like electrode 344 that are discharge electrodes of opposite polarities, and two annular induction electrodes that surround the respective discharge electrodes. A positive or negative high voltage is applied to each of first to fourth needle-like electrodes 341 to 344, and each of first to fourth needle-like electrodes 341 to 344 generates positive ions or negative ions.

Ion generation apparatuses 326 and 326 according to Comparative Example 2 described above were arranged in duct 15 having the same shape as that of duct 15 in FIG. 15 and at a position on the lower side in the height direction in duct 15. First needle-like electrode 341 generating the positive ions and third needle-like electrode 343 generating the negative ions were arranged such that needle tips thereof faced each other. Second needle-like electrode 342 generating the negative ions and fourth needle-like electrode 344 generating the positive ions were arranged such that needle tips thereof faced each other. Ion generation apparatuses 326 and 326 were arranged such that central axes of second needle-like electrode 342 and fourth needle-like electrode 344 were located at a position of 18 mm from an inner wall of duct 15 on the bottom surface side.

Each of the distance between the needle tip of first needle-like electrode 341 and the needle tip of third needle-like electrode 343 as well as the distance between the needle tip of second needle-like electrode 342 and the needle tip of fourth needle-like electrode 344 was set at 112 mm Each of the interval between the needle tip of first needle-like electrode 341 and the needle tip of second needle-like electrode 342 as well as the interval between the needle tip of third needle-like electrode 343 and the needle tip of fourth needle-like electrode 344 was set at 38 mm.

Table 1 summarizes an integrated value of measurement values of ion concentration in Comparative Example 1 and Example 1, with Comparative Example 1 being standardized as 100%. The ion concentration was measured at a position away from the electrodes by 350 mm on the downstream side (downwind side) of the air flow flowing through duct 15. Measurement was conducted at a total of nine grid-like measurement points, i.e., three points in the width direction of duct 15 at an interval of 100 mm, and three points in the height direction of duct 15 at an interval of 60 mm

TABLE 1

|  | Percentage of integrated value of amount of ions |
| --- | --- |
| Comparative Example 1 | 100 |
| Example 1 | 318 |

As shown in Table 1, the integrated value of the ion concentration at the nine measurement points in Example 1 was 318% of that in Comparative Example 1. From this result, it could be confirmed that ion generation apparatus 26 according to Example 1 can supply a larger amount of positive and negative ions as compared with ion generation apparatus 226 according to Comparative Example 1, and the sufficient number of positive and negative ions can be supplied to the vicinity of the outlet of ion generation apparatus 26.

Table 2 summarizes an integrated value of measurement values of ion concentration at the aforementioned nine measurement points in Comparative Example 2 and Example 1, with Comparative Example 1 being standardized as 100%.

TABLE 2

|  | Percentage of maximum positive ion concentration | Percentage of maximum negative ion concentration | Percentage of integrated value of amount of ions |
|---|---|---|---|
| Comparative Example 2 | 100 | 100 | 100 |
| Example 1 | 171 | 165 | 142 |

As shown in Table 2, the positive ion concentration at the nine measurement points in Example 1 was 171% of that in Comparative Example 1, the negative ion concentration at the nine measurement points in Example 1 was 165% of that in Comparative Example 1, and the integrated value of the ion concentration at the nine measurement points in Example 1 was 142% of that in Comparative Example 1. From this result, it could be confirmed that ion generation apparatus 26 according to Example 1 can supply a larger amount of positive and negative ions as compared with ion generation apparatus 326 according to Comparative Example 2, and the sufficient number of positive and negative ions can be supplied to the vicinity of the outlet of ion generation apparatus 26.

Table 3 summarizes an ion concentration at one measurement point in Examples 1 and 2 that is located away by 350 mm from the electrodes on the downstream side (downwind side) of the air flow flowing through duct 15 and at the center in the width direction of the inner wall of duct 15 on the bottom surface side, with Example 1 being set as 100%.

TABLE 3

|  | Percentage of positive ion concentration | Percentage of negative ion concentration |
|---|---|---|
| Example 1 | 100 | 100 |
| Example 2 | 101 | 103 |

As shown in Table 3, the positive ion concentration at one measurement point in Example 2 was 101% of that in Example 1, and the negative ion concentration at one measurement point in Example 2 was 103% of that in Example 1. From this result, it could be confirmed that in Example 2 as well in which induction electrode 45 is formed by the wiring pattern, a sufficient amount of ions equal to or larger than that in ion generation apparatus 26 according to Example 1 can be supplied.

Figure 19:
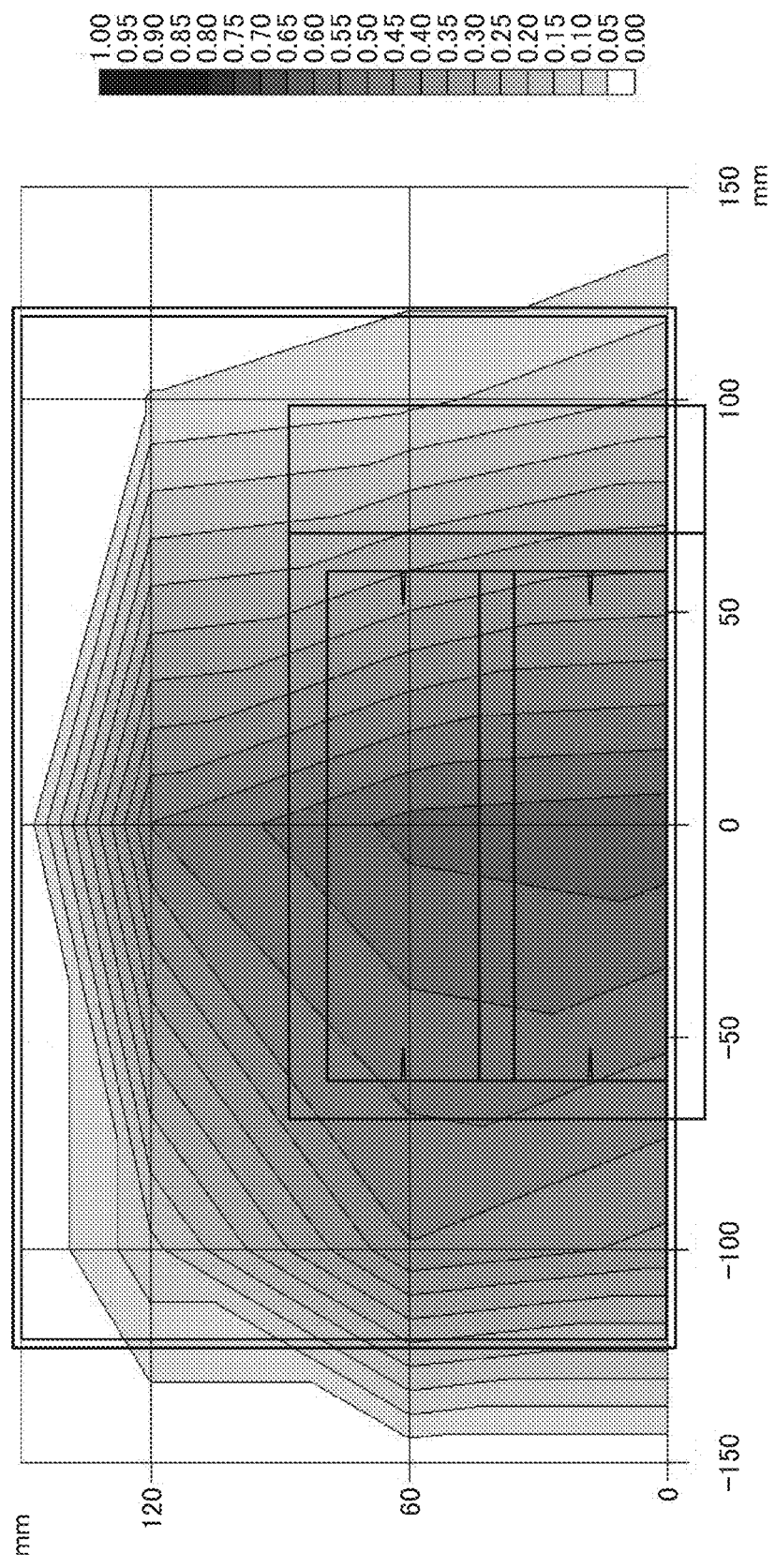
FIG. 19 is a schematic view showing an ion concentration distribution on the downstream side of the ion generation apparatus according to Example 1.
Figure 20:
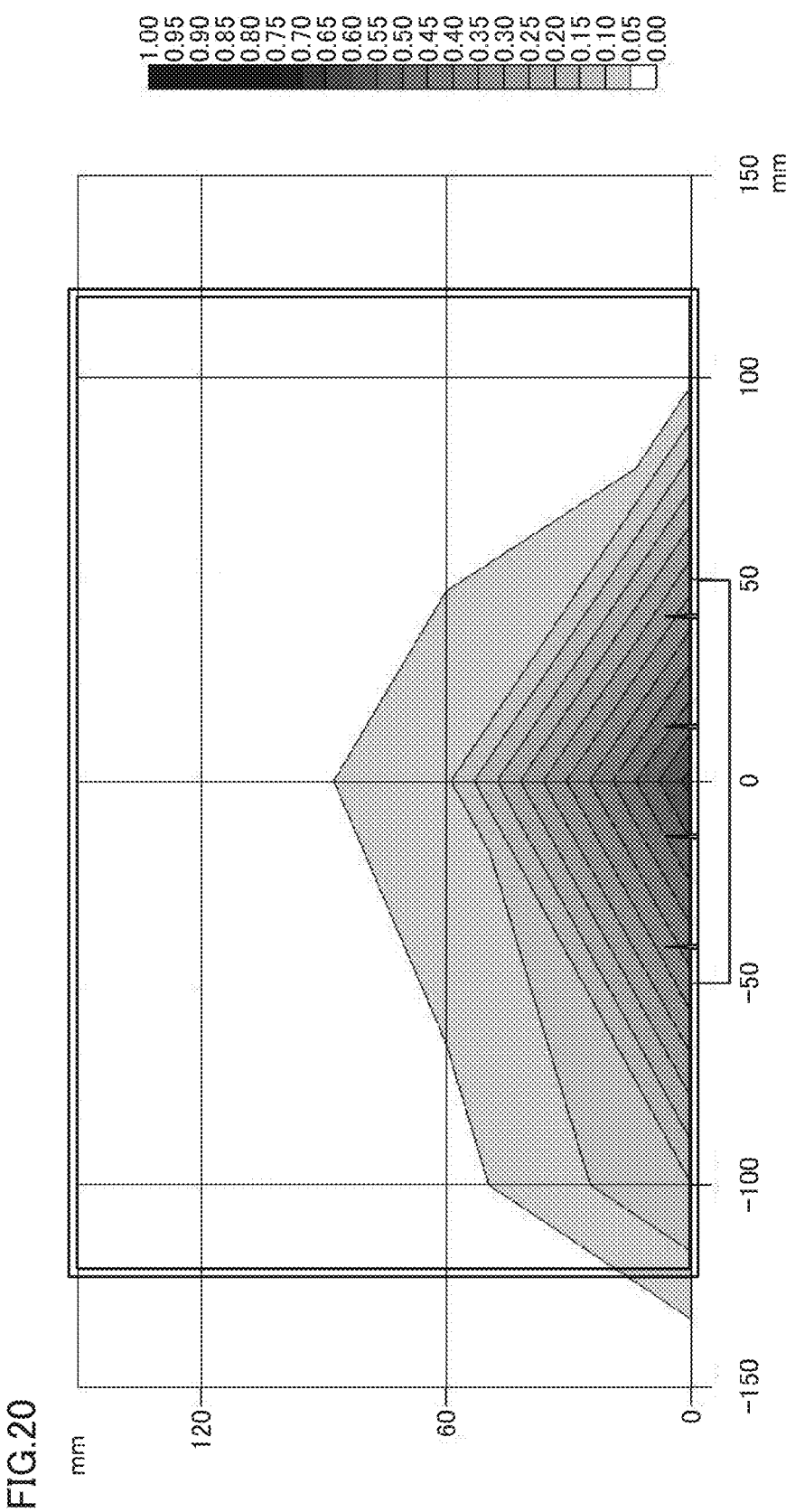
FIG. 20 is a schematic view showing an ion concentration distribution on the downstream side of the ion generation apparatus according to Comparative Example 1.
Figure 21:
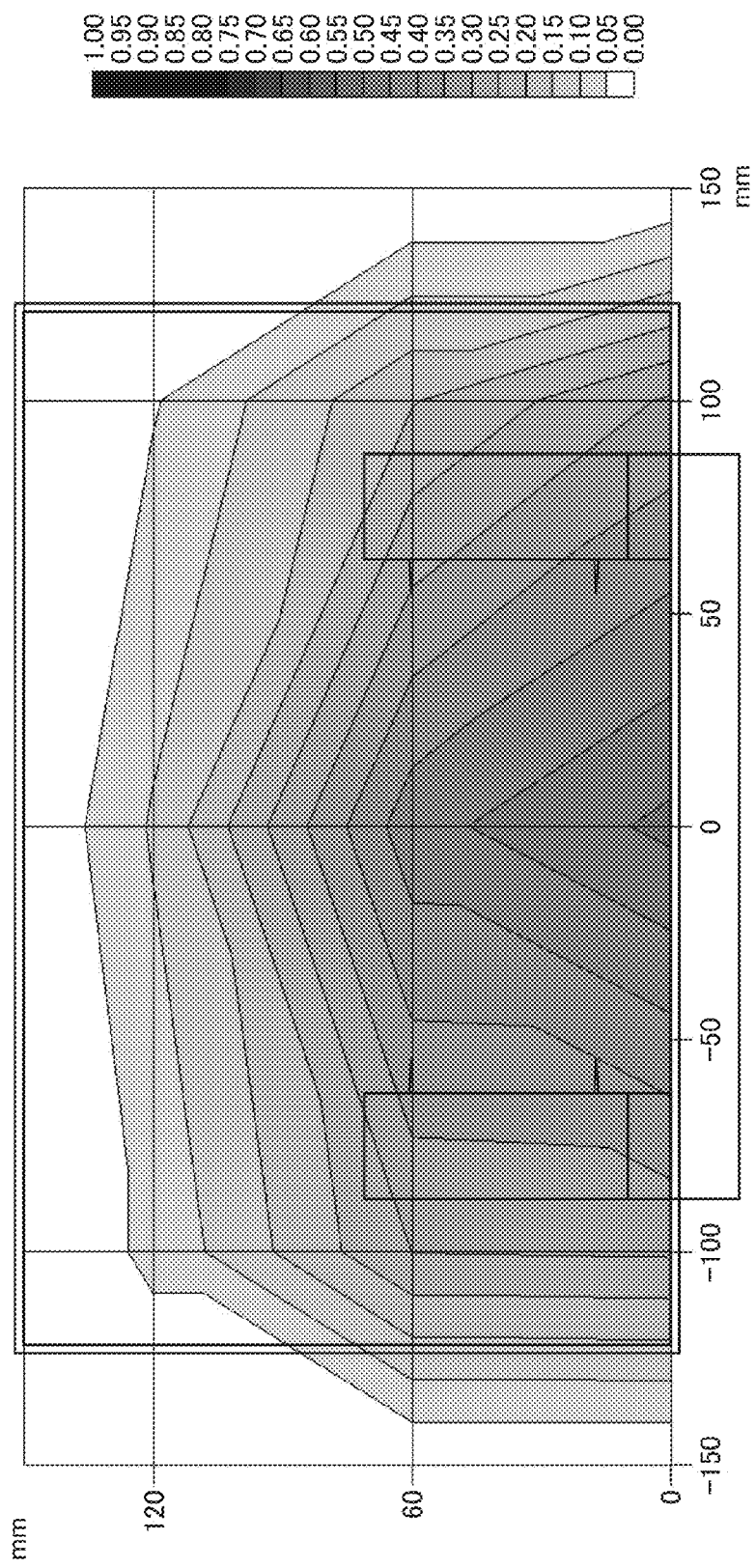
FIG. 21 is a schematic view showing an ion concentration distribution on the downstream side of the ion generation apparatus according to Comparative Example 2.

FIG. 19 is a schematic view showing an ion concentration distribution on the downstream side of ion generation apparatus 26 according to Example 1. FIG. 20 is a schematic view showing an ion concentration distribution on the downstream side of ion generation apparatus 26 according to Comparative Example 1. FIG. 21 is a schematic view showing an ion concentration distribution on the downstream side of ion generation apparatus 26 according to Comparative Example 2.

FIGS. 19 to 21 illustrate, as a graph, a distribution of the lower one of the positive ion concentration and the negative ion concentration (i.e., a distribution of the lower ion concentration when the positive and negative ions are both present) measured at a position away by 350 mm from the electrodes on the downstream side (downwind side) of the air flow flowing through duct 15 in Example 1 and Comparative Examples 1 and 2. In FIGS. 19 to 21, the vertical axis indicates a coordinate in the height direction of duct 15, the horizontal axis indicates a coordinate in the width direction of duct 15, and the standardized ion concentration is indicated by gradation of the graph. The center in the width direction of duct 15 and the inner wall on the bottom surface side in the height direction of duct 15 were set as 0 of a coordinate axis.

In Comparative Example 1 shown in FIG. 20, a high ion concentration was obtained near the center of the bottom surface of duct 15 provided with the four needle-like electrodes, while the ion concentration was low near a ceiling of duct 15 and on the right and left sides in the width direction of duct 15, and a range of presence of a high concentration of ions was small. In Comparative Example 2 shown in FIG. 21, the ions were present over a wider range than in Comparative Example 1. However, a maximum value of the ion concentration was smaller than that in Comparative Example 1.

In contrast, in Example 1 shown in FIG. 19, a region where the positive and negative ions were both present covered a wide range and the ion concentration was higher than that in Comparative Example 2. Namely, comparing Example 1 and Comparative Example 2 in terms of the ion concentration near the coordinate axis of 0, it turns out that in Example 1, there is a region where a higher concentration of positive ions and a higher concentration of negative ions are both present, as compared with Comparative Example 2. Therefore, it was shown that ion generation apparatus 26 according to Example 1 can supply the sufficient number of positive and negative ions and can cause a high concentration of positive and negative ions to be present over a wide range.

While the embodiments of the present invention have been described above, it should be understood that the embodiments and examples disclosed herein are illustrative and non-restrictive in every respect. The scope of the present invention is defined by the terms of the claims, rather than the description above, and is intended to include any modifications within the scope and meaning equivalent to the terms of the claims.

REFERENCE SIGNS LIST

10 air flow path; 12, 15, 17, 18 duct; 16 air blower; 26 ion generation apparatus; 31 outer case; 31*s* outer surface; 32, 33 substrate housing portion; 34, 35, 36 rib-like portion; 37 first wall surface; 38 space; 39 second wall surface; 40 discharge electrode; 41 first needle-like electrode; 42 second needle-like electrode; 43 third needle-like electrode; 44 fourth needle-like electrode; 45 induction electrode; 50 base member; 51, 52 substrate; 51*a*, 51*b*, 52*a* surface; 53 high voltage generation circuit portion; 54, 55 substrate supporting case; 56, 57 wiring; 90 boosting circuit; 91 boosting transformer; 91*a* primary winding; 91*b* secondary winding; 100 electric equipment; D1 first interval; D2 second interval; L distance; N negative ion; P positive ion; T1, T2 terminal.

The invention claimed is:

1. An ion generation apparatus, comprising:
    discharge electrodes including a first needle-like electrode, a second needle-like electrode, a third needle-like electrode, and a fourth needle-like electrode, each of which is arranged such that a direction of extension thereof is parallel and each of which generates ions by discharge; and
    an air flow path through which a gas for conveying the ions generated by said discharge electrodes flows, wherein
    needle tips of said first needle-like electrode and said second needle-like electrode protrude from a first wall surface that forms said air flow path, are spaced apart from each other by a first interval, and are arranged in line in said air flow path,
    needle tips of said third needle-like electrode and said fourth needle-like electrode protrude from a second wall surface that forms said air flow path and faces said first wall surface, are spaced apart from each other by a second interval, and are arranged in line in said air flow path,
    said first needle-like electrode and said fourth needle-like electrode generate positive ions, and said second needle-like electrode and said third needle-like electrode generate negative ions, and
    the first wall surface from which said first needle-like electrode and said second needle-like electrode protrude and the second wall surface from which said third needle-like electrode and said fourth needle-like electrode protrude are provided in different discontinuous planes which are directly opposed to one another with the air flow path provided therebetween, and the gas which flows through the air flow path passes directly through a space defined directly between the first wall surface and the second wall surface.

2. The ion generation apparatus according to claim 1, wherein
    the needle tip of said first needle-like electrode and the needle tip of said third needle-like electrode face each other.

3. The ion generation apparatus according to claim 2, wherein
    a distance between the needle tip of said first needle-like electrode and the needle tip of said third needle-like electrode is larger than said first interval and larger than said second interval.

4. The ion generation apparatus according to claim 2, wherein
    the needle tip of said second needle-like electrode and the needle tip of said fourth needle-like electrode face each other.

5. The ion generation apparatus according to claim 4, wherein
    a distance between the needle tip of said second needle-like electrode and the needle tip of said fourth needle-like electrode is larger than said first interval and larger than said second interval.

6. The ion generation apparatus according to claim 1, further comprising:
    a base member having said discharge electrodes mounted thereon; and
    a casing that houses said base member, wherein
    a part of an outer surface of said casing forms said first wall surface and said second wall surface, and said casing is provided such that said air flow path is formed between said first wall surface and said second wall surface.

7. The ion generation apparatus according to claim 1, further comprising
    an induction electrode arranged between said first needle-like electrode and said second needle-like electrode and at a distance from both said first needle-like electrode and said second needle-like electrode, wherein
    a distance between the needle tip of said third needle-like electrode and said induction electrode is larger than a distance between the needle tip of said first needle-like electrode and said induction electrode.

8. Electric equipment, comprising: the ion generation apparatus according to claim 1; and an air blower for blowing a gas into an air flow path of said ion generation apparatus.

9. An ion generation apparatus, comprising:
    an air flow path through which a gas flows;
    a first needle-like electrode and a second needle-like electrode protruding into said air flow path from a first wall surface that forms said air flow path, arranged to extend in a direction orthogonal to a gas flowing direction in said air flow path, and generating ions by discharge; and
    a third needle-like electrode and a fourth needle-like electrode protruding into said air flow path from a second wall surface that forms said air flow path and faces said first wall surface, arranged to extend in the direction orthogonal to the gas flowing direction in said air flow path, and generating ions by discharge, wherein
    the first wall surface from which said first needle-like electrode and said second needle-like electrode protrude and the second wall surface from which said third needle-like electrode and said fourth needle-like electrode protrude are provided in different discontinuous planes which are directly opposed to one another with the air flow path provided therebetween, and the gas which flows through the air flow path passes directly through a space defined directly between the first wall surface and the second wall surface,
    said first needle-like electrode and said second needle-like electrode are arranged such that needle tips thereof are spaced apart from each other by a first distance in the direction orthogonal to the gas flowing direction in said air flow path,
    said first needle-like electrode and said third needle-like electrode are arranged such that needle tips thereof face each other and are spaced apart from each other by a second distance in the direction orthogonal to the gas flowing direction in said air flow path, and
    on a downstream side of a gas flow with respect to said first to fourth needle-like electrodes, said air flow path causes said gas flow to branch off in a direction of the longer one of said first distance and said second distance.

10. The ion generation apparatus according to claim 9, wherein
    on the downstream side of the gas flow with respect to said first to fourth needle-like electrodes, said air flow path has a bifurcated duct bifurcated in the direction of the longer one of said first distance and said second distance.

11. The ion generation apparatus according to claim 9, wherein said air flow path is provided with an outlet through which the gas is blown out from said air flow path, said outlet has two sides extending in the direction of the longer one of said first distance and said second distance, and facing each other, said outlet is provided with adjustment plates extending from said two sides toward downstream of said gas flow, respectively, said adjustment plates are arranged to be inclined such that an interval therebetween becomes narrower toward downstream of said gas flow, and a width of said adjustment plates becomes narrower toward downstream of said gas flow, as compared with a width of portions of said adjustment plates that are in contact with said outlet.

12. The ion generation apparatus according to claim 9, further comprising a flow path dividing member for dividing an internal space of said air flow path, on the downstream side of said gas flow with respect to said first to fourth needle-like electrodes, and said flow path dividing member extends in a direction of the shorter one of said first distance and said second distance.

13. The ion generation apparatus according to claim 9, wherein one of the two needle-like electrodes that form the shorter one of said first distance and said second distance generates positive ions, and the other generates negative ions.

* * * * *